(12) United States Patent
Citron et al.

(10) Patent No.: US 7,579,180 B2
(45) Date of Patent: Aug. 25, 2009

(54) BETA SECRETASE POLYPEPTIDES

(75) Inventors: Martin Citron, Thousand Oaks, CA (US); Robert James Vassar, Westlake Village, CA (US); Brian Drake Bennett, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/680,476

(22) Filed: Feb. 28, 2007

(65) Prior Publication Data

US 2007/0173477 A1 Jul. 26, 2007

Related U.S. Application Data

(63) Continuation of application No. 09/277,229, filed on Mar. 26, 1999, now abandoned.

(51) Int. Cl.
*C12N 9/50* (2006.01)
*C12N 9/00* (2006.01)
*C12N 9/64* (2006.01)
*C12N 1/20* (2006.01)
*C12N 15/00* (2006.01)
*C07H 21/04* (2006.01)

(52) U.S. Cl. ............... 435/219; 435/183; 435/226; 435/252.3; 435/320.1; 536/23.2

(58) Field of Classification Search ............ 435/183, 435/219, 226, 252.3, 320.1; 536/23.2
See application file for complete search history.

(56) References Cited

U.S. PATENT DOCUMENTS

| | | | |
|---|---|---|---|
| 3,773,919 A | 11/1973 | Boswell et al. | |
| 4,816,567 A | 3/1989 | Cabilly et al. | |
| 4,892,538 A | 1/1990 | Aebischer et al. | |
| 4,945,050 A | 7/1990 | Sanford et al. | |
| 4,970,154 A | 11/1990 | Chang | |
| 5,011,472 A | 4/1991 | Aebischer et al. | |
| 5,106,627 A | 4/1992 | Aebischer et al. | |
| 5,272,071 A | 12/1993 | Chappel | |
| 5,364,791 A | 11/1994 | Vegeto et al. | |
| 5,399,346 A | 3/1995 | Anderson et al. | |
| 5,489,743 A | 2/1996 | Robinson et al. | |
| 5,557,032 A | 9/1996 | Mak | |
| 5,589,362 A | 12/1996 | Bujard et al. | |
| 5,593,875 A | 1/1997 | Wurm et al. | |
| 5,631,236 A | 5/1997 | Woo et al. | |
| 5,635,399 A | 6/1997 | Kriegler et al. | |
| 5,650,298 A | 7/1997 | Bujard et al. | |
| 5,654,168 A | 8/1997 | Bujard et al. | |
| 5,672,344 A | 9/1997 | Kelley et al. | |
| 5,672,510 A | 9/1997 | Eglitis et al. | |
| 5,676,954 A | 10/1997 | Brigham | |
| 5,679,559 A | 10/1997 | Kim et al. | |
| 5,744,346 A | 4/1998 | Chrysler et al. | |
| 6,319,689 B1 | 11/2001 | Powell et al. | |
| 6,420,534 B1 | 7/2002 | Gurney et al. | |
| 6,440,698 B1 | 8/2002 | Gurney et al. | |
| 6,500,667 B1 | 12/2002 | Gurney et al. | |
| 6,699,671 B1 | 3/2004 | Gurney et al. | |
| 6,706,485 B1 | 3/2004 | Gurney et al. | |
| 6,727,074 B2 | 4/2004 | Gurney et al. | |
| 6,737,510 B1 | 5/2004 | Gurney et al. | |
| 6,753,163 B2 | 6/2004 | Gurney et al. | |
| 6,790,610 B2 | 9/2004 | Gurney et al. | |
| 6,797,487 B2 | 9/2004 | Gurney et al. | |
| 6,825,023 B1 * | 11/2004 | Gurney et al. ............ 435/226 |
| 6,828,117 B2 * | 12/2004 | Gurney et al. ............ 435/23 |
| 6,835,565 B1 | 12/2004 | Gurney et al. | |
| 6,844,148 B1 | 1/2005 | Gurney et al. | |
| 6,867,018 B1 | 3/2005 | Gurney et al. | |
| 6,870,030 B2 | 3/2005 | Powell et al. | |
| 6,913,918 B2 | 7/2005 | Gurney et al. | |
| 7,041,473 B1 | 5/2006 | Gurney et al. | |
| 2002/0037315 A1 | 3/2002 | Gurney et al. | |
| 2002/0081634 A1 | 6/2002 | Gurney et al. | |
| 2003/0109022 A1 | 6/2003 | Powell et al. | |
| 2004/0043408 A1 | 3/2004 | Gurney et al. | |
| 2004/0048303 A1 | 3/2004 | Gurney et al. | |
| 2004/0166507 A1 | 8/2004 | Gurney et al. | |
| 2004/0234976 A1 | 11/2004 | Gurney et al. | |
| 2005/0026256 A1 | 2/2005 | Gurney et al. | |
| 2005/0080232 A1 | 4/2005 | Gurney et al. | |
| 2005/0101556 A1 | 5/2005 | Powell et al. | |
| 2005/0196398 A1 | 9/2005 | Gurney et al. | |
| 2006/0263852 A1 | 11/2006 | Powell et al. | |
| 2006/0269539 A1 | 11/2006 | Powell et al. | |

FOREIGN PATENT DOCUMENTS

| | | |
|---|---|---|
| EP | 0 133988 | 8/1984 |
| EP | 0 143949 | 6/1985 |
| EP | 0 067676 | 4/1986 |

(Continued)

OTHER PUBLICATIONS

Chica et al. Curr Opin Biotechnol. Aug. 2005;16(4):378-84.*

(Continued)

*Primary Examiner*—Christian L Fronda
(74) *Attorney, Agent, or Firm*—Nisan A. Steinberg

(57) ABSTRACT

Disclosed are novel genes encoding beta secretase polypeptides. Also disclosed are methods of making and using the polypeptides.

1 Claim, 15 Drawing Sheets

FOREIGN PATENT DOCUMENTS

| EP | 0 058481 | 10/1986 |
|---|---|---|
| EP | 0 088046 | 12/1987 |
| EP | 0 036676 | 9/1990 |
| EP | 0 505500 | 7/1997 |
| EP | 0 848062 | 6/1998 |
| EP | 0 855444 | 7/1998 |
| WO | WO 91/09955 | 7/1991 |
| WO | WO 91/10425 | 7/1991 |
| WO | WO 91/10470 | 7/1991 |
| WO | WO 93/15722 | 8/1993 |
| WO | WO 94/28122 | 12/1994 |
| WO | WO 95/05452 | 2/1995 |
| WO | WO 95/34670 | 12/1995 |
| WO | WO 96/37609 | 11/1996 |
| WO | WO 96/40958 | 12/1996 |
| WO | WO 96/41865 | 12/1996 |
| WO | WO 97/31899 | 9/1997 |
| WO | WO 98/26059 | 6/1998 |
| WO | WO 99/64587 | 12/1999 |
| WO | WO 00/17369 | 3/2000 |
| WO | WO 01/23533 | 4/2001 |
| WO | WO 01/49097 | 7/2001 |
| WO | WO 01/49098 | 7/2001 |
| WO | WO 01/50829 | 7/2001 |

OTHER PUBLICATIONS

Witkowski et al. Biochemistry. Sep. 7, 1999; 38(36): 11643-50.*
Seffernick et al. J Bacteriol. Apr. 2001; 183 (8): 2405-10.*
Alignment of SEQ ID No. 4 to US Patent 6,828,117, published Dec. 2004.*
Aebischer et al., "Long-Term Cross-Species Brain Transplantation of a Polymer-Encapsulated Dopamine-Secreting Cell Line", *Exper. Neurol.*, 111: 269-275 (1991).
Atschul et al., "Basic Local Alignment Search Tool", *J. Molec. Biol.* 215: 403-410 (1990).
Ausubel et al., *Current Protocols in Molecular Biology*, John Wiley & Sons (1994) (Table of Contents Provided).
Ausubel et al., "*Metal-Chelate Affinity Chromatography*" current *Protocols in Molecular Biology*, Section 10.11.8 (1993).
Baca et al. "Chemical Litigation of Cysteine-Containing Peptides: Synthesis of a 22 kDa", *J. Amer. Chem. soc.*, U117: 1881-1887 (1995).
Brodeur et al., *Monoclonal Antibody production Techniques and Applications*, "Mouse-Human Myeloma Partners for the Production of heterohybridomas" pp. 51-63 (1987), Marcel Dekker, Inc. N.Y.
Brüggermann et al., "Designer Mice: The Production of Human Antibody" Year *in Immuno*. 7: 33-44 (1993).
Chevallier et al., "Cathepsin D Displays In Vitro Beta-Secretase-Like Specificity" *Brain Research*, 750: 11-19 (1997).
Citron et al., "Mutation of the β-amyloid Precursor Protein in Familial Alzheimer's Disease Increases β-protein Production", *Nature*, 360: 672-674 (1992).
Citron et al., "Generation of Amyloid β Protein from its Precursor is Sequence Specific", *Neuron*, 14: 661-670 (1995).
Dayhoff et al., *Atlas of Protein Sequence and Structure*, 5: Supp.3 (1978) (Table of Contents Provided).
Devereaux et al., Nucleic Acids Research, 12: 387 (1984) (Table of Contents Provided).
Doetschan et al., "Targeted Correction of a Mutant HPRT Gene in Mouse Embryonic Stem Cells", *Nature*, 330: 576-578 (1987).
Doetschman et al., "Targeted Mutation of the HPRT Gene in Mouse Embryonic Stem Cells", *Proc. Natl. Acad. Sci.*, 85: 8583-8587 (1988).
Engels et al., "Gene Synthesis", *Angew. Chem. Intl. Ed.*, 28: 716-734 (1989).
Eppstein et al., "Biological Activity of Liposome-Encapsulated Murine Interferon y is Mediated by a Cell Membrane Receptor", *Proc. Natl. Acad. Sci. USA*, 82: 3688-3692 (1985) Cell Biology.
Gennaro, A. R., *Remington's Pharmaceutical Sciences, 18th Edition*, Mack Publishing company (1990) (Table of Contents Provided).
Gorman et al., "Transient Production pf Proteins Using and Adenovirus Transformed Cell Line" *DNA Prot. Eng. Tech.* 2: 3-10 (1990).
Gouras et al., *J. Neurochem.*, 71: 1920-1925 (1998).
Gribskov, et al., *Sequence Analysis Primer*, Oxford University Press (1992) (Table of Contents Provided).
Griffin, *Computer Analysis of Sequence Data, Part*1, Humana Press (1994) (Table of Contents Provided).
Hefti, J., "Neurotrophic Factor Therapy for Nervous System Degenerative Diseases", *Neurobiology*, 25: 1418-1435 (1994).
Henikoff et al., *Proc. Natl. Acad. Sci USA*, 89: 10915-10919 (1992).
Hoogenboom et al., "By-passing Immunisation Human Antibodies from Synthetic Repertories of Gemline $V_H$ Gene in Vitro", *J. Mol. Biol.*, 227: 381-388 (1992).
Houghten et al., "General Method for the Rapid Solid-phase Synthesis of Large Numbers of Peptides: Specificity of Antigen-antibody Interaction t the Level of Inidividual Amino Acids", *Proc. Natl. Acad. Sci. USA*, 82: 5132 (1985).
Huber, et al., "cDNA Cloning and Molecular Characterization of Human Brain Metalloprotease MP100: A Beta-Secretase Candidate?" *Journal of Neurochemistry*, 72: No. 3: 1215-1223 (1999).
Hussain, et al., "Identification of a Novel Aspartic Protease (Asp 2) as Beta Secretase", *Molecular and Cellular Neuroscience*, 14: No. 6: 419-427 (1999).
Jakobovits et al., "Germ-line Transmission and Expression of a Human-derived Yeast Artificial Chromosome", *Nature*, 362: 255-258 (1993).
Jakobovits et al., "Analysis of Homozygous Mutant Chimeric Mice: Deletion of the Immunoglobulin Heavy-chain joining Region Blocks B-cell Development and Antibody Production", *Proc. Natl. Acad. Sci.*, 90: 2551-2555 (1993).
Jones et al., Replacing the Complementarity-Determining Regions in a Human Antibody with those from a Mouse, *Nature*, 321: 522-525 (1986).
Kitts et al., "A Method for Producing Recombinant Baculovirus Expression Vectors at High Frequency", *Biotechniques*, 14: 810-817 (1993).
Köhler et al., "Continuous Cultures of Fused Cells Secreting Antibody of Predefined Specificity", *Nature*, 256: 495-497 (1975).
Kozbor, "A Human Hybrid Myeloma for production of Human Monocioal Antibodies", *J. Immunol.*, 133: 3001 (1984).
Kucherlapati, "Homologous Recombination in Mammalian Somatic Cells" *progress in Nucleic Acid Research and Molecular Biology*, 36: 301-310 (1989).
Langer et al., "Biocompatibility of Polymeric Delivery Systems for Macromolecules", *J. Biomed. Mater. Res.*, 15: 267-277 (1981).
Langer, et al., "Controlled Release of Macromolecules", *Chem. Tech.*, 12: 98-105 (1982).
Lesk, *Computational Molecular Biology*, Oxford University press (1998) (Table of Contents Provided).
Lucklow, "Baculovirus Systems for the Expression of Human Gene Products", *Current Opinion in Biotechnology*, 4: 564-572 (1993).
Lucklow et al., "Efficient Generation of Infectious Recombinant Baculovirus by Site-Specific Transposon-Mediated Insertion of Foreign Genes into a Baculovirus Genome Propagated in *Escherichia coli*", *Journal of Virology*, 67, No. 8: 4566-4579 (1993).
Marks et al., "By-passing Immunization Human Antibodies from V-gene Libraries Displayed on Phage", *J. Mol. Biol.*, 222: 581 (1991).
Marston et al., "Solubilization of Protein Aggregates", *Methods in Enzymology*, 182: 264-275 (1990).
Merrifield et al., "Solid Phase Peptide Synthesis, The Synthesis of Tetrapeptide", *J. Am. Chem. Soc.*, 85: 2149 (1963).
Morrison et al., "chimetric Human Antibody Molecules: Mouse Antigen-Binding Domains With Human Constant Region Domains" *Proc. Natl. Acad. Sci.*, 81: 6851-6855 (1984).
Mullan et al., "A Pathogenic Mutation for Probable Alzheimer's Disease in the APP Gene at the N-terminus of β-amyloid" *Nature Genetics*, 1: 345-347 (1992).
Needleman et al., "A General Method Applicable to the Search for Similarities in the Amino Acid Sequence of Two Proteins", *J. Mol. Biol.*, 48: 443-453 (1970).

Reichmann et al., "Reshaping Human Antibodies for Therapy", *Nature*, 332: 323-327 (Mar. 1988).

Sambrook et al., *Molecular Cloning: A Laboratory Manual*, Cold Spring Harbor Laboratory Press (1989) (Table of Contents Provided).

Schnolver et al., "In Situ Neutralization In Boc-Chemistry Solid Phase Peptide Synthesis", *Int. J. Peptide Protein Res.*, 40: 180-193 (1992).

Selkoe, "Alzheimer's Disease: Genotypes, Phenotype, and Treatments", *Science*, 275: 630-631 (1997).

Sinha, et al., "Purification and Cloning of Amyloid Precursor Protein Beta-Secretase from Human Brain", *Nature, GB, McMillan Journals Ltd.* London, 402: No. 6761: 537-540 (1999).

Sidman et al., "Controlled Release of Macromolecules and Pharmaceuticals from Synthetic Polypeptides Based on Glutamic Acid", *Biopolymers*, 22: 547-556 (1983).

Smith D. W., *Biocomputing: Informatics and Genome Projects*, Academic Press (1993) (Table of Contents Provided).

Stewart et al., *Solid Phase Peptide Synthesis, Second Edition*, Pierce Chemical Co. (1994) (Table of Contents Provided).

Thomas et al., "Site-Directed Mutagenesis by Gene Targeting in Mouse Embryo-Derived Stem Cells", *Cell*, 51: 503-512 (1987).

Thomas et al., "High Frequency Targeting of Genes to Specific Sites in the Mammalian Genome", *Cell*, 419-428 (1986).

Thompson, et al., "Expression and Characterization of Human β-Secretase Candidates Metalloendopeptidase MP78 and Cathespin D in β-APP-Overexpressing Cells", *Molecular Brain Research*, 48: No. 2: 206-214 (1997).

Vassar, et al., "β-Secretase Cleavage of Alzheimer's Amyloid Precursor Protein by the Transmembrane Aspatic Protease BACE", *Science*, 286: No. 5440, 735-741 (1999).

Verhoeyen et al., "Reshaping Human Antibodies: Grafting an Antilysozyme Activity", *Science*, 239: 1534-1536 (1988).

von Heinje, *Sequence Analysis in Molecular Biology*, Academic Press (1987) (Table of Contents Provided).

Winn et al., "behavioral Recovery Following Intratriatal Implantation of Microencapsulated PC12 Cells", *Exper. Neurol.*, 113: 322-329 (1991).

Yan et al., Membrane-Anchored Aspartyl protase with Alzheimer's Disease •—Secretase Activity, *Nature*, 402: No. 6761: 533-537 (1999).

Zola, *Monoclonal Antibodies: A Manual of Techniques*, pp. 147-158 (CRC press, Inc. (1987) (Table of Contents Provided).

Gurney et al., U.S. Patent 6797487, Alignment to SEQ ID No. 4, (Jan. 22, 2009).

* cited by examiner

FIG. 1A

```
ATGGCCCAAG CCCTGCCCTG GCTCCTGCTG TGGATGGGCG CGGGAGTGCT
GCCTGCCCAC GGCACCCAGC ACGGCATCCG GCTGCCCCTG CGCAGCGGCC
TGGGGGGCGC CCCCCTGGGG CTGCGGCTGC CCCGGGAGAC CGACGAAGAG
CCCGAGGAGC CCGGCCGGAG GGGCAGCTTT GTGGAGATGG TGGACAACCT
GAGGGGCAAG TCGGGGCAGG GCTACTACGT GGAGATGACC GTGGGCAGCC
CCCCGCAGAC GCTCAACATC CTGGTGGATA CAGGCAGCAG TAACTTTGCA
GTGGGTGCTG CCCCCCACCC CTTCCTGCAT CGCTACTACC AGAGGCAGCT
GTCCAGCACA TACCGGGACC TCCGGAAGGG TGTGTATGTG CCCTACACCC
AGGGCAAGTG GGAAGGGGAG CTGGGCACCG ACCTGGTAAG CATCCCCCAT
GGCCCCAACG TCACTGTGCG TGCCAACATT GCTGCCATCA CTGAATCAGA
CAAGTTCTTC ATCAACGGCT CCAACTGGGA AGGCATCCTG GGGCTGGCCT
ATGCTGAGAT TGCCAGGCCT GACGACTCCC TGGAGCCTTT CTTTGACTCT
CTGGTAAAGC AGACCCACGT TCCCAACCTC TTCTCCCTGC AGCTTTGTGG
TGCTGGCTTC CCCCTCAACC AGTCTGAAGT GCTGGCCTCT GTCGGAGGA
GCATGATCAT TGGAGGTATC GACCACTCGC TGTACACAGG CAGTCTCTGG
TATACACCCA TCCGGCGGGA GTGGTATTAT GAGGTGATCA TTGTGCGGGT
GGAGATCAAT GGACAGGATC TGAAAATGGA CTGCAAGGAG TACAACTATG
ACAAGAGCAT TGTGGACAGT GGCACCACCA ACCTTCGTTT GCCCAAGAAA
GTGTTTGAAG CTGCAGTCAA ATCCATCAAG GCAGCCTCCT CCACGGAGAA
GTTCCCTGAT GGTTTCTGGC TAGGAGAGCA GCTGGTGTGC TGGCAAGCAG
GCACCACCCC TTGGAACATT TTCCCAGTCA TCTCACTCTA CCTAATGGGT
GAGGTTACCA ACCAGTCCTT CCGCATCACC ATCCTTCCGC AGCAATACCT
GCGGCCAGTG GAAGATGTGG CCACGTCCCA AGACGACTGT TACAAGTTTG
```

FIG. 1B

CCATCTCACA GTCATCCACG GGCACTGTTA TGGGAGCTGT TATCATGGAG

GGCTTCTACG TTGTCTTTGA TCGGGCCCGA AAACGAATTG GCTTTGCTGT

CAGCGCTTGC CATGTGCACG ATGAGTTCAG GACGGCAGCG GTGGAAGGCC

CTTTTGTCAC CTTGGACATG GAAGACTGTG GCTACAACAT TCCACAGACA

GATGAGTCAA CCCTCATGAC CATAGCCTAT GTCATGGCTG CCATCTGCGC

CCTCTTCATG CTGCCACTCT GCCTCATGGT GTGTCAGTGG CGCTGCCTCC

GCTGCCTGCG CCAGCAGCAT GATGACTTTG CTGATGACAT CTCCCTGCTG

AAG

FIG. 2A

```
ATGGCCCCAG CGCTGCACTG GCTCCTGCTA TGGGTGGGCT CGGGAATGCT
GCCTGCCCAG GGAACCCATC TCGGCATCCG GCTGCCCCTT CGCAGCGGCC
TGGCAGGGCC ACCCCTGGGC CTGAGGCTGC CCCGGGAGAC CGACGAGGAA
TCGGAGGAGC CTGGCCGGAG AGGCAGCTTT GTGGAGATGG TGGACAACCT
GAGGGGAAAG TCCGGCCAGG GCTACTATGT GGAGATGACC GTAGGCAGCC
CCCACAGAC GCTCAACATC CTGGTGGACA CGGGCAGTAG TAACTTTGCA
GTGGGGCTG CCCCACACCC TTTCCTGCAT CGCTACTACC AGAGGCAGCT
GTCCAGCACA TATCGAGACC TCCGAAAGGG TGTGTATGTG CCCTACACCC
AGGGCAAGTG GGAGGGGGAA CTGGGCACCG ACCTGGTGAG CATCCCTCAT
GGCCCCAACG TCACTGTGCG TGCCAACATT GCTGCCATCA CTGAATCGGA
CAAGTTCTTC ATCAATGGTT CCAACTGGGA GGGCATCCTA GGGCTGGCCT
ATGCTGAGAT TGCCAGGCCC GACGACTCTT TGGAGCCCTT CTTTGACTCC
CTGGTGAAGC AGACCCACAT TCCCAACATC TTTTCCCTGC AGCTCTGTGG
CGCTGGCTTC CCCCTCAACC AGACCGAGGC ACTGGCCTCG GTGGGAGGGA
GCATGATCAT TGGTGGTATC GACCACTCGC TATACACGGG CAGTCTCTGG
TACACACCCA TCCGGCGGGA GTGGTATTAT GAAGTGATCA TTGTACGTGT
GGAAATCAAT GGTCAAGATC TCAAGATGGA CTGCAAGGAG TACAACTACG
ACAAGAGCAT TGTGGACAGT GGGACCACCA ACCTTCGCTT GCCCAAGAAA
GTATTTGAAG CTGCCGTCAA GTCCATCAAG GCAGCCTCCT CGACGGAGAA
GTTCCCGGAT GGCTTTTGGC TAGGGGAGCA GCTGGTGTGC TGGCAAGCAG
GCACGACCCC TTGGAACATT TTCCCAGTCA TTTCACTTTA CCTCATGGGT
GAAGTCACCA ATCAGTCCTT CCGCATCACC ATCCTTCCTC AGCAATACCT
ACGGCCGGTG GAGGACGTGG CCACGTCCCA AGACGACTGT TACAAGTTCG
CTGTCTCACA GTCATCCACG GGCACTGTTA TGGGAGCCGT CATCATGGAA
```

FIG. 2B

GGTTTCTATG TCGTCTTCGA TCGAGCCCGA AAGCGAATTG GCTTTGCTGT

CAGCGCTTGC CATGTGCACG ATGAGTTCAG GACGGCGGCA GTGGAAGGTC

CGTTTGTTAC GGCAGACATG GAAGACTGTG GCTACAACAT TCCCCAGACA

GATGAGTCAA CACTTATGAC CATAGCCTAT GTCATGGCGG CCATCTGCGC

CCTCTTCATG TTGCCACTCT GCCTCATGGT ATGTCAGTGG CGCTGCCTGC

GTTGCCTGCG CCACCAGCAC GATGACTTTG CTGATGACAT CTCCCTGCTC

AAG

FIG. 3A

```
ATGGCCCCGG CGCTGCGCTG GCTCCTGCTA TGGGTGGGCT CGGGAATGCT
GCCTGCCCAG GGAACCCATC TCGGTATCCG ACTGCCCCTT CGCAGCGGCC
TGGCAGGGCC ACCCCTGGGC CTGAGGCTGC CCCGGGAGAC GGACGAGGAA
CCTGAGGAGC CTGGCCGGAG AGGCAGCTTT GTGGAGATGG TGGACAACCT
GAGGGGAAAG TCCGGCCAGG GCTACTATGT GGAGATGACC GTGGGCAGCC
CCCCACAGAC GCTCAACATC CTGGTGGACA CGGGCAGTAG TAATTTTGCA
GTGGGGGCTG CCCCACACCC TTTCCTGCAT CGATACTACC AAAGGCAGCT
GTCCAGTACA TACCGAGACC TCCGAAAGTC TGTGTATGTG CCCTACACCC
AGGGCAAGTG GGAGGGGGAA CTGGGCACTG ACCTGGTGAG CATCCCTCAT
GGCCCCAACG TCACTGTGCG TGCCAACATT GCTGCCATCA CTGAATCGGA
CAAGTTCTTC ATCAATGGTT CCAACTGGGA GGGCATCCTA GGGCTGGCCT
ATGCTGAGAT TGCCAGGCCT GACGACTCCT TGGAGCCCTT TTTTGACTCC
CTGGTGAAGC AGACCCACAT TCCGAACATC TTTTCCCTGC AGCTCTGTGG
CGCTGGCTTC CCCCTCAACC AGACTGAGGC ACTGGCCTCG GTGGGAGGGA
GCATGATCAT TGGTGGTATC GACCATTCCC TATACACTGG CAGTCTCTGG
TACACACCCA TCCGGCGGGA GTGGTATTAT GAAGTGATCA TTGTACGTGT
AGAAATCAAT GGTCAAGATC TGAAAATGGA CTGCAAGGAG TACAACTATG
ACAAGAGCAT CGTGGACAGT GGCACCACCA ACCTTCGTTT GCCCAAGAAA
GTATTTGAAG CTGCAGTCAA GTCCATCAAG GCAGCCTCCT CGACGGAGAA
GTTCCCGGAT GGCTTTTGGC TAGGGGAGCA GCTGGTGTGC TGGCAAGCAG
GCACGACCCC TTGGAACATT TTCCCAGTCA TTTCACTTTA CCTCATGGGT
GAAGTCACCA ATCAGTCCTT CCGCATCACC ATCCTTCCTC AGCAATACCT
ACGGCCAGTG GAAGATGTGG CCACGTCCCA AGACGACTGT TACAAGTTCG
```

FIG. 3B

CCGTCTCACA GTCATCCACA GGCACCGTTA TGGGAGCGGT CATCATGGAA

GGCTTCTATG TGGTCTTTGA TCGAGCCCGA AAGCGAATTG GCTTTGCTGT

CAGCGCTTGC CATGTGCACG ATGAGTTCAG GACGGCGGCA GTGGAAGGTC

CGTTTGTCAC GGCAGACATG GAAGACTGTG GCTACAACAT TCCACAGACA

GATGAGTCAA CACTTATGAC CATAGCCTAT GTCATGGCTG CCATCTGCGC

CCTCTTCATG TTGCCACTCT GCCTCATGGT ATGTCAGTGG CGCTGCCTAC

GCTGCCTGCG CCATCAGCAT GATGACTTTG CTGATGACAT CTCCCTGCTG

AAA

FIG. 4

```
MAQALPWLLL WMGAGVLPAH GTQHGIRLPL RSGLGGAPLG LRLPRETDEE
PEEPGRRGSF VEMVDNLRGK SGQGYYVEMT VGSPPQTLNI LVDTGSSNFA
VGAAPHPFLH RYYQRQLSST YRDLRKGVYV PYTQGKWEGE LGTDLVSIPH
GPNVTVRANI AAITESDKFF INGSNWEGIL GLAYAEIARP DDSLEPFFDS
LVKQTHVPNL FSLQLCGAGF PLNQSEVLAS VGGSMIIGGI DHSLYTGSLW
YTPIRREWYY EVIIVRVEIN GQDLKMDCKE YNYDKSIVDS GTTNLRLPKK
VFEAAVKSIK AASSTEKFPD GFWLGEQLVC WQAGTTPWNI FPVISLYLMG
EVTNQSFRIT ILPQQYLRPV EDVATSQDDC YKFAISQSST GTVMGAVIME
GFYVVFDRAR KRIGFAVSAC HVHDEFRTAA VEGPFVTLDM EDCGYNIPQT
DESTLMTIAY VMAAICALFM LPLCLMVCQW RCLRCLRQQH DDFADDISLL
K
```

FIG. 5

```
MAPALHWLLL WVGSGMLPAQ GTHLGIRLPL RSGLAGPPLG LRLPRETDEE
SEEPGRRGSF VEMVDNLRGK SGQGYYVEMT VGSPPQTLNI LVDTGSSNFA
VGAAPHPFLH RYYQRQLSST YRDLRKGVYV PYTQGKWEGE LGTDLVSIPH
GPNVTVRANI AAITESDKFF INGSNWEGIL GLAYAEIARP DDSLEPFFDS
LVKQTHIPNI FSLQLCGAGF PLNQTEALAS VGGSMIIGGI DHSLYTGSLW
YTPIRREWYY EVIIVRVEIN GQDLKMDCKE YNYDKSIVDS GTTNLRLPKK
VFEAAVKSIK AASSTEKFPD GFWLGEQLVC WQAGTTPWNI FPVISLYLMG
EVTNQSFRIT ILPQQYLRPV EDVATSQDDC YKFAVSQSST GTVMGAVIME
GFYVVFDRAR KRIGFAVSAC HVHDEFRTAA VEGPFVTADM EDCGYNIPQT
DESTLMTIAY VMAAICALFM LPLCLMVCQW RCLRCLRHQH DDFADDISLL
K
```

FIG. 6

MAPALRWLLL WVGSGMLPAQ GTHLGIRLPL RSGLAGPPLG LRLPRETDEE
PEEPGRRGSF VEMVDNLRGK SGQGYYVEMT VGSPPQTLNI LVDTGSSNFA
VGAAPHPFLH RYYQRQLSST YRDLRKSVYV PYTQGKWEGE LGTDLVSIPH
GPNVTVRANI AAITESDKFF INGSNWEGIL GLAYAEIARP DDSLEPFFDS
LVKQTHIPNI FSLQLCGAGF PLNQTEALAS VGGSMIIGGI DHSLYTGSLW
YTPIRREWYY EVIIVRVEIN GQDLKMDCKE YNYDKSIVDS GTTNLRLPKK
VFEAAVKSIK AASSTEKFPD GFWLGEQLVC WQAGTTPWNI FPVISLYLMG
EVTNQSFRIT ILPQQYLRPV EDVATSQDDC YKFAVSQSST GTVMGAVIME
GFYVVFDRAR KRIGFAVSAC HVHDEFRTAA VEGPFVTADM EDCGYNIPQT
DESTLMTIAY VMAAICALFM LPLCLMVCQW RCLRCLRHQH DDFADDISLL
K

SEQUENCE LISTING

```
<160> NUMBER OF SEQ ID NOS: 26

<210> SEQ ID NO 1
<211> LENGTH: 1503
<212> TYPE: DNA
<213> ORGANISM: Homo sapiens

<400> SEQUENCE: 1
atggcccaag ccctgccctg gctcctgctg tggatgggcg cgggagtgct gcctgcccac      60
ggcacccagc acggcatccg gctgccccctg cgcagcggcc tgggggggcgc cccccctgggg     120 ctgcggctgc cccgggagac cgacgaagag cccgaggagc ccggccggag gggcagcttt     180
gtggagatgg tggacaacct gaggggcaag tcggggcagg gctactacgt ggagatgacc     240
gtgggcagcc ccccgcagac gctcaacatc ctggtggata caggcagcag taactttgca     300
```

-continued

```
gtgggtgctg cccccaccc cttcctgcat cgctactacc agaggcagct gtccagcaca      360
taccgggacc tccggaaggg tgtgtatgtg ccctacaccc agggcaagtg ggaaggggag      420
ctgggcaccg acctggtaag catcccccat ggccccaacg tcactgtgcg tgccaacatt      480
gctgccatca ctgaatcaga caagttcttc atcaacggct ccaactggga aggcatcctg      540
gggctggcct atgctgagat tgccaggcct gacgactccc tggagccttt ctttgactct      600
ctggtaaagc agacccacgt tcccaacctc ttctccctgc agctttgtgg tgctggcttc      660
cccctcaacc agtctgaagt gctggcctct gtcggaggga gcatgatcat tggaggtatc      720
gaccactcgc tgtacacagg cagtctctgg tatacaccca tccggcggga gtggtattat      780
gaggtgatca ttgtgcgggt ggagatcaat ggacaggatc tgaaaatgga ctgcaaggag      840
tacaactatg acaagagcat tgtggacagt ggcaccacca accttcgttt gcccaagaaa      900
gtgtttgaag ctgcagtcaa atccatcaag gcagcctcct ccacggagaa gttccctgat      960
ggtttctggc taggagagca gctggtgtgc tggcaagcag gcaccacccc ttggaacatt     1020
ttcccagtca tctcactcta cctaatgggt gaggttacca accagtcctt ccgcatcacc     1080
atccttccgc agcaatacct gcggccagtg aagatgtgg ccacgtccca agacgactgt      1140
tacaagtttg ccatctcaca gtcatccacg ggcactgtta tgggagctgt tatcatggag     1200
ggcttctacg ttgtctttga tcgggcccga aaacgaattg ctttgctgt cagcgcttgc      1260
catgtgcacg atgagttcag gacggcagcg gtggaaggcc ttttgtcac cttggacatg     1320
gaagactgtg gctacaacat tccacagaca gatgagtcaa ccctcatgac catagcctat     1380
gtcatggctg ccatctgcgc cctcttcatg ctgccactct gcctcatggt tgtcagtgg      1440
cgctgcctcc gctgcctgcg ccagcagcat gatgactttg ctgatgacat ctccctgctg     1500
aag                                                                    1503
```

<210> SEQ ID NO 2
<211> LENGTH: 1503
<212> TYPE: DNA
<213> ORGANISM: Mus musculus

<400> SEQUENCE: 2

```
atggccccag cgctgcactg gctcctgcta tgggtgggct cgggaatgct gcctgcccag       60
ggaacccatc tcggcatccg gctgcccctt cgcagcggcc tggcagggcc acccctgggc      120
ctgaggctgc cccgggagac cgacgaggaa tcggaggagc tggccggaga ggcagctt      180
gtggagatgg tggacaacct gaggggaaag tccggccagg gctactatgt ggagatgacc      240
gtaggcagcc cccacagac gctcaacatc ctggtggaca cggcagtag taactttgca      300
gtgggggctg cccacaccc tttcctgcat cgctactacc agaggcagct gtccagcaca      360
tatcgagacc tccgaaaggg tgtgtatgtg ccctacaccc agggcaagtg ggaggggaa      420
ctgggcaccg acctggtgag catccctcat ggccccaacg tcactgtgcg tgccaacatt      480
gctgccatca ctgaatcgga caagttcttc atcaatggtt ccaactggga gggcatccta      540
gggctggcct atgctgagat tgccaggccc gacgactctt tggagccctt ctttgactcc      600
ctggtgaagc agacccacat tcccaacatc ttttccctgc agctctgtgg cgctggcttc      660
cccctcaacc agaccgaggc actggcctcg gtgggaggga gcatgatcat tggtggtatc      720
gaccactcgc tatacacggg cagtctctgg tacacaccca tccggcggga gtggtattat      780
gaagtgatca ttgtacgtgt ggaaatcaat ggtcaagatc tcaagatgga ctgcaaggag      840
```

| | |
|---|---|
| tacaactacg acaagagcat tgtggacagt gggaccacca accttcgctt gcccaagaaa | 900 |
| gtatttgaag ctgccgtcaa gtccatcaag gcagcctcct cgacggagaa gttcccggat | 960 |
| ggcttttggc tagggagca gctggtgtgc tggcaagcag gcacgacccc ttggaacatt | 1020 |
| ttcccagtca tttcacttta cctcatgggt gaagtcacca atcagtcctt ccgcatcacc | 1080 |
| atccttcctc agcaatacct acggccggtg gaggacgtgg ccacgtccca agacgactgt | 1140 |
| tacaagttcg ctgtctcaca gtcatccacg ggcactgtta gggagccgt catcatggaa | 1200 |
| ggtttctatg tcgtcttcga tcgagcccga aagcgaattg ctttgctgt cagcgcttgc | 1260 |
| catgtgcacg atgagttcag gacggcggca gtggaaggtc cgtttgttac ggcagacatg | 1320 |
| gaagactgtg gctacaacat tccccagaca gatgagtcaa cacttatgac catagcctat | 1380 |
| gtcatggcgg ccatctgcgc cctcttcatg ttgccactct gcctcatggt atgtcagtgg | 1440 |
| cgctgcctgc gttgcctgcg ccaccagcac gatgactttg ctgatgacat ctccctgctc | 1500 |
| aag | 1503 |

<210> SEQ ID NO 3
<211> LENGTH: 1503
<212> TYPE: DNA
<213> ORGANISM: Rattus rattus

<400> SEQUENCE: 3

| | |
|---|---|
| atggccccgg cgctgcgctg gctcctgcta tgggtgggct cgggaatgct gcctgcccag | 60 |
| ggaacccatc tcggtatccg actgccccct cgcagcggcc tggcagggcc acccctgggc | 120 |
| ctgaggctgc cccgggagac ggacgaggaa cctgaggagc ctggccggag aggcagcttt | 180 |
| gtggagatgg tggacaacct gaggggaaag tccggccagg gctactatgt ggagatgacc | 240 |
| gtgggcagcc ccccacagac gctcaacatc ctggtggaca cgggcagtag taattttgca | 300 |
| gtggggggctg ccccacaccc tttcctgcat cgatactacc aaaggcagct gtccagtaca | 360 |
| taccgagacc tccgaaagtc tgtgtatgtg ccctacaccc agggcaagtg ggaggggaa | 420 |
| ctgggcactg acctggtgag catccctcat ggccccaacg tcactgtgcg tgccaacatt | 480 |
| gctgccatca ctgaatcgga caagttcttc atcaatggtt ccaactggga gggcatccta | 540 |
| gggctggcct atgctgagat tgccaggcct gacgactcct tggagccctt ttttgactcc | 600 |
| ctggtgaagc agacccacat tccgaacatc ttttcccctgc agctctgtgg cgctggcttc | 660 |
| cccctcaacc agactgaggc actggcctcg gtgggaggga gcatgatcat tggtggtatc | 720 |
| gaccattccc tatacactgg cagtctctgg tacacaccca tccggcggga gtggtattat | 780 |
| gaagtgatca ttgtacgtgt agaaatcaat ggtcaagatc tgaaaatgga ctgcaaggag | 840 |
| tacaactatg caagagcat cgtggacagt ggcaccacca accttcgttt gcccaagaaa | 900 |
| gtatttgaag ctgcagtcaa gtccatcaag gcagcctcct cgacggagaa gttcccggat | 960 |
| ggcttttggc tagggagca gctggtgtgc tggcaagcag gcacgacccc ttggaacatt | 1020 |
| ttcccagtca tttcacttta cctcatgggt gaagtcacca atcagtcctt ccgcatcacc | 1080 |
| atccttcctc agcaatacct acggccagtg gaagatgtgg ccacgtccca agacgactgt | 1140 |
| tacaagttcg ccgtctcaca gtcatccaca ggcaccgtta gggagcggt catcatggaa | 1200 |
| ggcttctatg tggtctttga tcgagcccga aagcgaattg ctttgctgt cagcgcttgc | 1260 |
| catgtgcacg atgagttcag gacggcggca gtggaaggtc cgtttgtcac ggcagacatg | 1320 |
| gaagactgtg gctacaacat tccacagaca gatgagtcaa cacttatgac catagcctat | 1380 |
| gtcatggctg ccatctgcgc cctcttcatg ttgccactct gcctcatggt atgtcagtgg | 1440 |

```
cgctgcctac gctgcctgcg ccatcagcat gatgactttg ctgatgacat ctccctgctg   1500
aaa                                                                   1503

<210> SEQ ID NO 4
<211> LENGTH: 501
<212> TYPE: PRT
<213> ORGANISM: Homo sapiens

<400> SEQUENCE: 4

Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350
```

```
Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
        370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 5
<211> LENGTH: 501
<212> TYPE: PRT
<213> ORGANISM: Mus musculus

<400> SEQUENCE: 5

Met Ala Pro Ala Leu His Trp Leu Leu Leu Trp Val Gly Ser Gly Met
  1               5                  10                  15

Leu Pro Ala Gln Gly Thr His Leu Gly Ile Arg Leu Pro Leu Arg Ser
             20                  25                  30

Gly Leu Ala Gly Pro Pro Leu Gly Leu Arg Leu Pro Arg Glu Thr Asp
         35                  40                  45

Glu Glu Ser Glu Glu Pro Gly Arg Arg Gly Ser Phe Val Glu Met Val
     50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
    210                 215                 220
```

```
Thr Glu Ala Leu Ala Ser Val Gly Gly Ser Met Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Val Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Ala Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg His Gln His Asp Asp Phe Ala Asp Asp
                485                 490                 495

Ile Ser Leu Leu Lys
            500

<210> SEQ ID NO 6
<211> LENGTH: 501
<212> TYPE: PRT
<213> ORGANISM: Rattus rattus

<400> SEQUENCE: 6

Met Ala Pro Ala Leu Arg Trp Leu Leu Leu Trp Val Gly Ser Gly Met
1               5                   10                  15

Leu Pro Ala Gln Gly Thr His Leu Gly Ile Arg Leu Pro Leu Arg Ser
                20                  25                  30

Gly Leu Ala Gly Pro Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
```

```
                85                  90                  95
Ser Asn Phe Ala Val Gly Ala Pro His Pro Phe Leu His Arg Tyr
            100                 105                 110
Tyr Gln Arg Gln Leu Ser Ser Thr Tyr Arg Asp Leu Arg Lys Ser Val
            115                 120                 125
Tyr Val Pro Tyr Thr Gln Gly Lys Trp Glu Gly Glu Leu Gly Thr Asp
    130                 135                 140
Leu Val Ser Ile Pro His Gly Pro Asn Val Thr Val Arg Ala Asn Ile
145                 150                 155                 160
Ala Ala Ile Thr Glu Ser Asp Lys Phe Phe Ile Asn Gly Ser Asn Trp
                165                 170                 175
Glu Gly Ile Leu Gly Leu Ala Tyr Ala Glu Ile Ala Arg Pro Asp Asp
            180                 185                 190
Ser Leu Glu Pro Phe Phe Asp Ser Leu Val Lys Gln Thr His Ile Pro
        195                 200                 205
Asn Ile Phe Ser Leu Gln Leu Cys Gly Ala Gly Phe Pro Leu Asn Gln
    210                 215                 220
Thr Glu Ala Leu Ala Ser Val Gly Gly Ser Met Ile Ile Gly Gly Ile
225                 230                 235                 240
Asp His Ser Leu Tyr Thr Gly Ser Leu Trp Tyr Thr Pro Ile Arg Arg
                245                 250                 255
Glu Trp Tyr Tyr Glu Val Ile Ile Val Arg Val Glu Ile Asn Gly Gln
            260                 265                 270
Asp Leu Lys Met Asp Cys Lys Glu Tyr Asn Tyr Asp Lys Ser Ile Val
        275                 280                 285
Asp Ser Gly Thr Thr Asn Leu Arg Leu Pro Lys Lys Val Phe Glu Ala
    290                 295                 300
Ala Val Lys Ser Ile Lys Ala Ala Ser Ser Thr Glu Lys Phe Pro Asp
305                 310                 315                 320
Gly Phe Trp Leu Gly Glu Gln Leu Val Cys Trp Gln Ala Gly Thr Thr
                325                 330                 335
Pro Trp Asn Ile Phe Pro Val Ile Ser Leu Tyr Leu Met Gly Glu Val
            340                 345                 350
Thr Asn Gln Ser Phe Arg Ile Thr Ile Leu Pro Gln Gln Tyr Leu Arg
        355                 360                 365
Pro Val Glu Asp Val Ala Thr Ser Gln Asp Asp Cys Tyr Lys Phe Ala
    370                 375                 380
Val Ser Gln Ser Ser Thr Gly Thr Val Met Gly Ala Val Ile Met Glu
385                 390                 395                 400
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Ala Asp Met Glu Asp Cys Gly Tyr Asn Ile Pro
        435                 440                 445
Gln Thr Asp Glu Ser Thr Leu Met Thr Ile Ala Tyr Val Met Ala Ala
    450                 455                 460
Ile Cys Ala Leu Phe Met Leu Pro Leu Cys Leu Met Val Cys Gln Trp
465                 470                 475                 480
Arg Cys Leu Arg Cys Leu Arg His Gln His Asp Asp Phe Ala Asp Asp
                485                 490                 495
Ile Ser Leu Leu Lys
            500
```

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Leu Arg Gln Gln His Asp Asp Phe Ala Asp Asp Ile Ser Leu Leu
 1               5                  10                  15

Lys

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tgactctctg gtaaagcaga ccca                                          24

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
aggcacgtcg taagggtact tcagcaggga gatgtca                            37

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
tgaagatctt catccgctgg cataatcagg cacgtcgtaa gggta                   45

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gtgccgatgt agcgggctcc gga                                           23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12

```
ctgctgcctg tagccaccag gatg                                              24
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13

```
catcctggtg gctacaggca gcag                                              24
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14

```
cacccgcaca atgatcacct cataa                                             25
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15

```
gtgccgatgt agcgggctcc gga                                               23
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16

```
cacccgcaca atgatcacct cataa                                             25
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Val Asn Leu Asp Ala Glu Phe
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Val Lys Met Asp Ala Glu Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Lys Val Asp Ala Glu Phe
 1               5

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
cgggatccgg tcaccgacaa aactcacaca                                    30

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gctctagaag cttctgcagg tcgactcatt tacccggaga                         40

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
cgaccactcg ctgtacacag gcag                                          24

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
gtcggtgacc gcataggcta tggtcatgag ggt                                33

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Glu Val Asn Leu
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Val Lys Val
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Val Lys Met
  1
```

BETA SECRETASE POLYPEPTIDES

CROSS REFERENCE TO RELATED APPLICATIONS

This application is a continuation of U.S. application Ser. No. 09/277,229 filed Mar. 26, 1999, now abandoned, which is hereby incorporated by reference in its entirety.

FIELD OF THE INVENTION

The present invention relates to novel beta secretase polypeptides and nucleic acid molecules encoding the polypeptides. The invention also relates to vectors, host cells, antibodies and methods for producing beta secretase polypeptides.

BACKGROUND OF THE INVENTION

Patients with Alzheimer's disease initially show short term memory loss. As the disease progresses, the patients become completely demented. The brains of Alzheimer's patients contain numerous amyloid plaques and neurofibrillary tangles (highly insoluble protein aggregates). Not surprisingly, such plaques and tangles are found primarily in those regions of the brain involved with memory and cognition.

The amyloid plaques are associated with dystrophic dendrites and axons, as well as activated microglia and reactive astrocytes. The major component of the plaques is a peptide referred to as A-beta (Selkoe, *Science*, 275:630-631 [1997]).

A-beta is ultimately generated by endoprotease cleavages of the polypeptide beta-amyloid precursor protein (beta-APP) Beta-APP is constitutively expressed in most cells of the body, but production of A-beta appears to be highest in brain cells. A-beta is typically secreted by the cells that produce it into the extracellular matrix where it makes its way into various bodily fluids. A schematic diagram of beta-APP processing is set forth in FIG. 12.

There are three major isoforms of beta-APP polypeptide, and they are referred to as beta-APP695, beta-APP751 and beta-APP770. The number on each isoform refers to the number of amino acids it contains.

Beta-APP is synthesized as a membrane protein and spans the Golgi membrane. Normal non-pathogenic processing of beta-APP is believed to occur via a putative enzyme referred to as "alpha-secretase". Alpha-secretase cleaves between amino acids 687 and 688 of beta-APP770 (or between amino acids 612 and 613 of beta-APP695), thereby generating a 687 amino acid soluble form of beta-APP770 (or a 612 amino acid soluble form of beta-APP695) referred to as "alpha-APPs". The remaining membrane-bound portion of beta-APP (amino acids 688-770 of the beta-APP770 isoform) is cleaved by the enzyme gamma-secretase. Gamma secretase cleaves between amino acids 711 and 712, and between amino acids 713 and 714, to generate the fragments 688-711, 688-713, and 712-770 and 714-770. The first two fragments are referred to as "p3" and are released from the membrane. Gamma secretase is also active on the two other isoforms of beta-APP.

In both non-diseased people and Alzheimer's disease patients, beta-APP is also processed via an alternative mechanism. Here, a heretofore uncharacterized enzyme referred to as "beta-secretase" cleaves full length beta-APP between amino acids 671 and 672 of beta-APP770, thereby generating a soluble fragment of amino acids 1-671, referred to as "beta-APPs" and a membrane bound form of amino acids 672-770. The membrane bound form is then acted on by gamma secretase which, as mentioned above, cleaves between amino acids 711 and 712, and between amino acids 713 and 714 to produce soluble fragments of amino acids 672-711 and 672-713; these fragments are referred to as "A-beta 40", and "A-beta 42", respectively. In addition, gamma secretase activity generates membrane bound fragments of amino acids 712-770 and 714-770. A-beta 40 and A-beta 42 are secreted from the cells and accumulate in the brains of Alzheimer's patients to form the characteristic brain tissue plaques.

Recent evidence suggests that beta secretase can also cleave beta-APP between amino acids 683 and 684 of the 770 isoform (Gouras et al., *J. Neurochem.*, 71:1920-1925 [1998]) thereby ultimately generating a second form of A-beta spanning amino acids 684-711 and 684-713. The mechanisms that control this alternate cleavage are not known.

A few naturally occurring mutations of beta-APP have been identified. These include the so called "Swedish mutation" in which amino acids 670 and 671 of the 770 isoform are mutated, and the London mutation in which amino acid 717 of the 770 isoform is mutated. The Swedish mutation, which causes familial Alzheimer's disease, has been found to result in increased A-beta production in vivo (Citron et al., *Nature*, 360:672-674 [1992]; see also Citron et al., *Neuron*, 14:661-670 [1995]).

U.S. Pat. No. 5,744,346 purportedly describes a beta secretase molecule. No nucleic acid sequence or amino acid sequence for this molecule is presented.

European patent application EP 0 855 444 A2 published 29 Jul. 1998 describes an aspartic proteinase that purportedly plays a role in Alzheimer's disease. This aspartic proteinase has sequence similarity at both the nucleic acid and amino acid levels to the beta-secretase of the present invention.

European patent application EP 0 848 062 A2, published 17 Jun. 1998, describes an aspartic proteinase termed "ASP1" which has approximately 47 percent identity at the amino acid level to the prepro form of the beta-secretase of the present invention as determined by a computer comparison using the GAP alignment program.

Accordingly, it is an object of the invention to identify nucleic acid molecules encoding beta secretase polypeptides. Such molecules have use as probes for diagnosis of Alzheimer's disease, and for identification of compounds that modulate the activity of beta secretase.

SUMMARY OF THE INVENTION

The invention provides an isolated nucleic acid molecule selected from the group consisting of:

a) the nucleic acid molecule as set forth in any of SEQ ID NOS: 1, 2, and 3;

b) a nucleic acid molecule encoding the polypeptide of any of SEQ ID NOS: 4, 5, and 6;

c) biologically active fragments of SEQ ID NO:4;

d) an allelic variant or splice variant of any of (a) or (b);

e) a nucleic acid molecule of the DNA vector insert in ATCC Deposit No. 207158;

f) a nucleic acid molecule of the DNA vector insert in ATCC Deposit No. 207159;

g) a nucleic acid molecule encoding a polypeptide having one to fifty conservative amino acid substitutions as compared with the polypeptide of SEQ ID NO:4, wherein the polypeptide encoded by said nucleic acid molecule is biologically active; and h) a nucleic acid molecule that is the complement of any of (a)-(g) above.

In other embodiments, the invention provides expression vectors, host cells, and methods of preparing recombinant beta secretase polypeptide.

The invention also provides an isolated polypeptide selected from the group consisting of:
a) the polypeptide of any of SEQ ID NOS: 4, 5, and 6;
b) a biologically active fragment of any of SEQ ID NOS. 4, 5, 6;
c) a biologically active polypeptide having one to fifty conservative amino acid changes as compared with the polypeptide of SEQ ID NO:4;
d) the polypeptide encoded by the DNA vector insert of ATCC Deposit Nos. 207158 and 207159; and
e) a polypeptide that is an allelic variant or splice variant of (a).

The invention further provides an isolated beta secretase polypeptide fragment of SEQ ID NO:4 selected from the group consisting of: amino acids 46-501; amino acids 46-460; amino acids 45-460; amino acids 1-460; amino acids 93-292; amino acids 93-293; amino acids 91-295; amino acids 90-295; amino acids 90-300; amino acids 280-310; amino acids 62-420; amino acids 1-420; amino acids 62-460; amino acids 90-460; amino acids 62-501; amino acids 62-460; amino acids 93-293; amino acids 90-293; amino acids 90-300; amino acids 62-420; amino acids 62-501; amino acids 1-420; amino acids 46-420; amino acids 62-420; amino acids 73-420; amino acids 83-420; amino acids 90-420; amino acids 62-417; amino acids 73-417; amino acids 83-417; amino acids 90-417; amino acids 62-410; amino acids 73-410; amino acids 83-410; amino acids 90-4104; amino acids 62-402; amino acids 73-402; amino acids 83-402; and amino acids 90-40.

The invention further provides an antibody or fragment thereof specifically binding to beta secretase polypeptide.

The invention yet further provides a fusion polypeptide comprising full length or truncated beta-secretase polypeptide fused to a heterologous amino acid sequence such as the Fc portion of human IgG.

DESCRIPTION OF THE FIGURES

FIGS. 1A and 1B depict the cDNA sequence of human beta secretase (SEQ ID NO:1).

FIGS. 2A and 2B depict the cDNA sequence of mouse beta secretase (SEQ ID NO:2).

FIGS. 3A and 3B depict the cDNA sequence of rat beta secretase (SEQ ID NO:3).

FIG. 4 depicts the putative amino acid sequence of human beta secretase polypeptide (SEQ ID NO:4).

FIG. 5 depicts the putative amino acid sequence of mouse beta secretase polypeptide (SEQ ID NO:5).

FIG. 6 depicts the putative amino acid sequence of rat beta secretase polypeptide (SEQ ID NO:6).

DETAILED DESCRIPTION OF THE INVENTION

Figure 7:
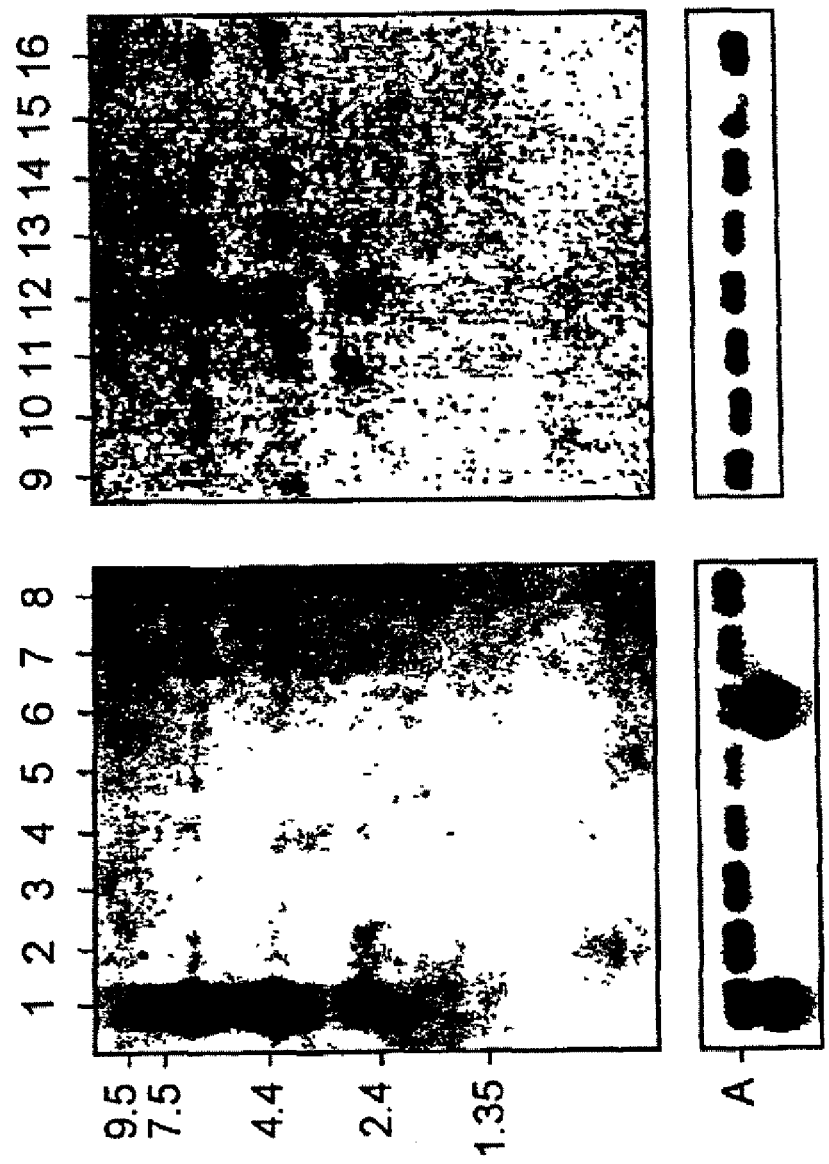
FIG. 7 depicts a human multiple tissue Northern blot which was probed with a PstI DNA fragment of human beta-secretase cDNA extending from nucleotide 318 to nucleotide 1090. Lane 1 is pancreas; Lane 2 is kidney; Lane 3 is skeletal muscle; Lane 4 is liver; Lane 5 is lung; Lane 6 is placenta; Lane 7 is brain; Lane 8 is heart; Lane 9 is peripheral blood leukocytes; Lane 10 is colon; Lane 11 is small intestine; Lane 12 is ovary; Lane 13 is spinal cord; Lane 14 is prostate; Lane 15 is thymus; Lane 16 is spleen. The lower panel shows a control hybridization using a DNA probe for actin. RNA size markers (in kb) are indicated on the left.

The section headings herein are for organizational purposes only and are not to be construed as limiting the subject matter described therein.

Definitions

The term "beta secretase nucleic acid molecule" refers to a nucleic acid molecule comprising or consisting essentially of a nucleotide sequence as set forth in any of SEQ ID NOS: 1, 2, and 3, comprising or consisting essentially of a nucleotide sequence encoding any of the polypeptides as set forth in SEQ ID NOS: 4, 5, and 6, comprising or consisting essentially of a nucleotide sequence of the DNA insert in ATCC deposit number 207158 and ATCC deposit number 207159 (both deposited 11 Mar. 1999), or nucleic acid molecules related thereto. Related nucleic acid molecules comprise or consist essentially of nucleotide sequences that are at least 70 percent identical to the nucleotide sequence as shown in any of SEQ ID NOS: 1, 2, and 3, or comprise or consist essentially of nucleotide sequences encoding polypeptides that are at least 70 percent identical to any of the polypeptides as set forth in SEQ ID NOS: 4, 5, and 6. The nucleotide sequences may be at least 75 percent, or about 80 percent, or about 85 percent, or about 90 percent, or about 95 percent identical to any of the nucleotide sequences as shown in SEQ ID NOS: 1, 2, and 3, or the nucleotide sequences that encode polypeptides that are about 75 percent, or about 80 percent, or about 85 percent, or about 90 percent, or about 95 percent identical to any of the polypeptide sequences as set forth in SEQ ID NOS 4, 5, and 6. Related nucleic acid molecules also include fragments of the above beta secretase nucleic acid molecules which are at least about 10 contiguous nucleotides, or about 15, or about 20, or about 25, or about 50, or about 75, or about 100, or greater than about 100 contiguous nucleotides. Related nucleic acid molecules also include fragments of the above beta secretase nucleic acid molecules which encode polypeptides of at least about 25 amino acid residues, or about 50, or about 75, or about 100, or greater than about 100 amino acid residues. Related beta secretase nucleic acid molecules include those molecules which comprise nucleotide sequences which hybridize under moderate or highly stringent conditions as defined herein with any of the above nucleic acid molecules. In preferred embodiments, the related nucleic acid molecules comprise sequences which hybridize under moderate or highly stringent conditions with the sequence as shown in SEQ ID NO:1, or with a molecule encoding a polypeptide, which polypeptide comprises the sequence as shown in SEQ ID NO:4, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "isolated nucleic acid molecule" refers to a nucleic acid molecule of the invention that is free from at least one contaminating nucleic acid molecule with which it is naturally associated, and preferably substantially free from any other contaminating mammalian nucleic acid molecules which would interfere with its use in protein production or its therapeutic or diagnostic use.

The term "allelic variant" refers to one of several possible naturally occurring alternate forms of a gene occupying a given locus on a chromosome of an organism.

The term "splice variant" refers to a nucleic acid molecule, usually RNA, which is generated by alternative processing of intron sequences in an RNA transcript.

The term "expression vector" refers to a vector which is suitable for propagation in a host cell and contains nucleic acid sequences which direct and/or control the expression of inserted heterologous nucleic acid sequences. Expression includes, but is not limited to, processes such as transcription, translation, and RNA splicing, if introns are present.

The term "high stringency conditions" refers to those conditions that (1) employ low ionic strength reagents and high temperature for washing, for example, 0.015 M NaCl/0.0015 M sodium citrate/0.1% NaDodSO4 (SDS) at 50° C., or (2) employ during hybridization a denaturing agent such as formamide, for example, 50% (vol/vol) formamide with 0.1% bovine serum albumin/0.1%. Alternatively, _Ficoll/0.1% polyvinylpyrrolidone/50 mM sodium phosphate buffer at pH 6.5 may be used with 750 mm NaCl, 75 mm sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS.

The term "moderate stringency conditions" refers to conditions which generally include the use of a washing solution and hybridization conditions (e.g., temperature, ionic strength, and percent SDS) less stringent than described above. An example of moderately stringent conditions are conditions such as overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 μl/ml denatured sheared salmon sperm DNA, followed by washing the filters in 1×SSC at about 37-50° C. The skilled artisan will recognize how to adjust the temperature, ionic strength etc. as necessary to accommodate factors such as probe length and the like.

Where oligonucleotide probes are used to screen cDNA or genomic libraries, one of the following two high stringency solutions may be used. The first of these is 6×SSC with 0.05 percent sodium pyrophosphate at a temperature of 35° C.-62° C., depending on the length of the oligonucleotide probe. For example, 14 base pair probes are washed at 35-40° C., 17 base pair probes are washed at 45-50° C., 20 base pair probes are washed at 52-57° C., and 23 base pair probes are washed at 57-63° C. The temperature can be increased 2-3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45-50° C.

The term "beta secretase polypeptide" refers to a polypeptide comprising the amino acid sequence of any of SEQ ID NOS: 4, 5, and 6, and related polypeptides described herein. Related polypeptides includes allelic variants, splice variants, fragments, derivatives, substitution, deletion, and insertion variants, fusion polypeptides, and orthologs. Beta secretase polypeptides may be processed polypeptides, i.e., not containing an endogenous or exogenous signal or leader sequence as defined herein, and may or may not have an amino terminal methionine residue, depending on the method by which they are prepared.

The term "mature beta-secretase polypeptide" refers to a polypeptide of any of SEQ ID NOS: 4, 5 and 6 and related polypeptides described herein, in which the leader sequence and the propeptide have been removed. Mature human beta-secretase is amino acids 46-501 of SEQ ID NO:4. For human beta-secretase, the leader peptide is amino acids 1-21 of SEQ ID NO:4, and the propeptide is amino acids 22-45 of SEQ ID NO:4.

The term "beta secretase polypeptide fragment" refers to a peptide or polypeptide that comprises less than the full length amino acid sequence of an beta secretase polypeptide as set forth in any of SEQ ID NOS: 4, 5, and 6. Such a fragment may arise, for example, from a truncation at the amino terminus, a truncation at the carboxy terminus, and/or an internal deletion of a residue(s) from the amino acid sequence. Naturally occurring beta secretase fragments may result from alternative RNA splicing, from in vivo processing such as removal of the leader peptide and propeptide, and/or from protease activity.

The term "beta secretase polypeptide variants" refers to beta secretase polypeptides comprising amino acid sequences which contain one or more amino acid sequence substitutions, deletions, and/or additions as compared to the beta secretase polypeptide amino acid sequence set forth in any of SEQ ID NOS: 4, 5, and 6 or fragments thereof. Variants may be naturally occurring or artificially constructed. Such beta secretase polypeptide variants may be prepared from the corresponding nucleic acid molecules encoding said variants, which have a DNA sequence that varies accordingly from the DNA sequences for wild type beta secretase polypeptides as set forth in any of SEQ ID NOS: 4, 5, and 6.

The term "beta secretase fusion polypeptide" refers to a fusion of beta secretase polypeptide, fragment, variant and/or derivative thereof, with a heterologous peptide or polypeptide.

The term "beta secretase polypeptide derivatives" refers to beta secretase polypeptides, variants, or fragments thereof, that have been chemically modified, as for example, by covalent attachment of one or more water soluble polymers, N-linked or O-linked carbohydrates, sugars, phosphates, and/or other such molecules. The derivatives are modified in a manner that is different from naturally occurring beta secretase, either in the type and/or location of the molecules attached to the polypeptide Derivatives further include the deletion of one or more chemical groups naturally attached to the beta secretase polypeptide.

The terms "biologically active beta secretase polypeptides", "biologically active beta secretase polypeptide fragments" "biologically active beta secretase polypeptide variants", and "biologically active beta secretase polypeptide derivatives" refer to beta secretase polypeptides having at least one activity characteristic of a beta secretase polypeptide, such as the ability to cleave the APP Swedish mutation peptide EVKMDAEF (SEQ ID NO:18) between the methionine and aspartic acid residues.

The term "isolated polypeptide" refers to a polypeptide of the invention that is free from at least one contaminating polypeptide that is found in its natural environment, and preferably substantially free from any other contaminating mammalian polypeptides which would interfere with its therapeutic or diagnostic use.

The term "ortholog" refers to a polypeptide that corresponds to a polypeptide identified from a different species. For example, mouse and human beta secretase polypeptides are considered orthologs.

The terms "effective amount" and "therapeutically effective amount" refer to the amount of a beta secretase polypeptide that is useful or necessary to support an observable level one or more biological activities of the beta secretase polypeptides as set forth above.

Relatedness of Nucleic Acid Molecules and/or Polypeptides

The term "identity", as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model or computer programs (i.e., "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, $10/20$ identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% ($15/20$). Therefore, in cases where there are conservative substitutions, the degree of similarity between two polypeptide sequences will be higher than the percent identity between those two sequences.

The term "conservative amino acid substitution" refers to a substitution of a native amino acid residue with a normative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine, as has been previously described for "alanine scanning mutagenesis". General classes of amino acids useful for conservative amino acid substitutions are set forth in Table I.

TABLE I

| Conservative Amino Acid Substitutions | |
|---|---|
| Basic: | arginine |
|  | lysine |
|  | histidine |
| Acidic: | glutamic acid |
|  | aspartic acid |
| Uncharged Polar: | glutamine |
|  | asparagine |
|  | serine |
|  | threonine |
|  | tyrosine |
| Non-Polar: | phenylalanine |
|  | tryptophan |
|  | cysteine |
|  | glycine |
|  | alanine |
|  | valine |
|  | proline |
|  | methionine |
|  | leucine |
|  | norleucine |
|  | isoleucine |

Conservative modifications to the amino acid sequence (and the corresponding modifications to the encoding nucleotides) are expected to produce beta secretase having functional and chemical characteristics similar to those of naturally occurring beta secretase.

Conservative amino acid substitutions also encompass non-naturally occurring amino acid residues which are typically incorporated by chemical peptide synthesis rather than by synthesis in biological systems. Such conservative amino acids include, for example, the "homolog" of each amino acid, where the homolog is an amino acid with a methylene group (CH2) inserted into the side chain at the beta position of that side chain.

Beta-secretase polypeptides of the present invention may have 1, 2, 3, 4, 5, 6, 7, 8, 9, 10, 11, 12, 13, 14, 15, 20, 25, 30, 35, 40, 45, 50, or up to 55 conservative amino acid changes as compared with the beta-secretase polypeptide of SEQ ID NO:4. Such molecules may also have chemical modifications as described herein for beta-secretase variants.

In contrast, non-conservative substitutions of beta secretase may be generated by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Non-conservative substitutions may involve the exchange of a member of one of the amino acid classes of Table I for a member from another class. Such substituted residues may be introduced into regions of the human beta secretase molecule that are homologous with non-human beta secretase, or into the non-homologous regions of the molecule.

Identity and similarity of related nucleic acid molecules and polypeptides can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 19933; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M. Stockton Press, New York, 1991; and Carillo, H., and Lipman, D., *SIAM J. Applied Math.*, 48:1073 (1988).

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux, et al., *Nucleic Acids Research* 12:387 [1984]; Genetics Computer Group, University of Wisconsin, Madison, Wis.), BLASTP, BLASTN, and FASTA (Atschul et al., *J. Molec. Biol.* 215: 403-410 [1990]). The BLAST X program is publicly available from the National Center for Biotechnology Information (NCBI) and other sources (BLAST Manual, Altschul] et al., NCB NLM NIH Bethesda, Md. 20894; Altschul et al., *J. Mol. Biol.* 215:403-410 [1990]). The well known Smith Waterman algorithm may also be used to determine identity.

By way of example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. A standard comparison matrix (see Dayhoff et al., in: Atlas of Protein Sequence and Structure, vol. 5, supp. 3 [1978] for the PAM250 comparison matrix; see Henikoff et al., *Proc. Natl. Acad. Sci USA*, 89:10915-10919 [1992] for the BLOSUM 62 comparison matrix) is also used by the algorithm.

Preferred parameters for polypeptide sequence comparison include the following:
Algorithm: Needleman and Wunsch, *J. Mol. Biol.* 48:443-453 (1970)
Comparison matrix: BLOSUM 62 from Henikoff and Henikoff, *Proc. Natl. Acad. Sci. USA* 89:10915-10919 (1992)
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, *J. Mol Biol.* 48:443-453 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

Recombinant DNA methods used herein are generally those set forth in Sambrook et al. (*Molecular Cloning: A Laboratory Manual*, Cold Spring Harbor Laboratory Press, Cold Spring Harbor, N.Y. [1989]) and/or Ausubel et al., eds., (*Current Protocols in Molecular Biology*, Green Publishers Inc. and Wiley and Sons, NY [1994]).

The invention provides for nucleic acid molecules as described herein and methods for obtaining the molecules. A gene or cDNA encoding a beta secretase polypeptide or fragment thereof may be obtained by hybridization screening of a genomic or cDNA library, or by PCR amplification. Probes or primers useful for screening a library by hybridization can be generated based on sequence information for other known genes or gene fragments from the same or a related family of genes, such as, for example, conserved motifs. In addition, where a gene encoding beta secretase polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the beta secretase gene. In addition, part or all of a nucleic acid molecule having any of the sequences as set forth in SEQ ID NOS: 1, 2, and 3 may be used to screen a genomic library to identify and isolate a gene encoding beta secretase. Typically, conditions of moderate or high stringency will be employed for screening to minimize the number of false positives obtained from the screen.

Nucleic acid molecules encoding beta secretase polypeptides may also be identified by expression cloning which employs detection of positive clones based upon a property of the expressed protein. Typically, nucleic acid libraries are screened by binding of an antibody or other binding partner (e.g., receptor or ligand) to cloned proteins which are expressed and displayed on the host cell surface. The antibody or binding partner is modified with a detectable label to identify those cells expressing the desired clone.

Another means of preparing a nucleic acid molecule encoding a beta secretase polypeptide or fragment thereof is chemical synthesis using methods well known to the skilled artisan such as those described by Engels et al. (*Angew. Chem. Intl. Ed.*, 28:716-734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the beta secretase polypeptide will be several hundred nucleotides in length. Nucleic acids larger than about 100 nucleotides can be synthesized as several fragments using these methods. The fragments can then be ligated together to form the full length beta secretase polypeptide. Usually, the DNA fragment encoding the amino terminus of the polypeptide will have an ATG, which encodes a methionine residue. This methionine may or may not be present on the mature form of the beta secretase polypeptide, depending on whether the polypeptide produced in the host cell is designed to be secreted from that cell.

In some cases, it may be desirable to prepare nucleic acid molecules encoding beta secretase polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In one embodiment, nucleic acid molecule variants contain codons which have been altered for optimal expression of an beta secretase polypeptide in a given host cell. Particular codon alterations will depend upon the beta secretase polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh. Cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high.cod".

In other embodiments, nucleic acid molecules encode beta secretase variants with conservative amino acid substitutions as defined above, beta secretase variants comprising an addition and/or a deletion of one or more N-linked or O-linked glycosylation sites, or beta secretase polypeptide fragments as described above. In addition, nucleic acid molecules may encode any combination of beta secretase variants, fragments, and fusion polypeptides described herein.

Preferred nucleic acid molecule fragments encode the following fragments of SEQ ID NO:4: amino acids 45-501; amino acids 46-501; amino acids 46-460; amino acids 45-460; amino acids 1-460; amino acids 93-292; amino acids 93-293; amino acids 91-295; amino acids 90-295; amino acids 90-300; amino acids 62-420; amino acids 1-420; amino acids 62-460; amino acids 90-460; amino acids 62-501; amino acids 62-460; amino acids 90-293; amino acids 90-300; amino acids 1-420; amino acids 46-420; amino acids 62-420; amino acids 73-420; amino acids 83-420; amino acids 90-420; amino acids 62-417; amino acids 73-417; amino acids 83-417; amino acids 90-417; amino acids 62-410; amino acids 73-410; amino acids 83-410; amino acids 90-410; amino acids 62-402; amino acids 73-402; amino acids 83-402; and amino acids 90-402.

Additionally preferred nucleic acid molecule fragments include nucleic acid molecules encoding each of the foregoing fragments joined to a nucleic acid molecule encoding a peptide or polypeptide such as, for example, the Fc portion of human IgG.

Vectors and Host Cells

A nucleic acid molecule encoding a beta secretase polypeptide can be inserted into an appropriate expression vector in order to generate beta secretase polypeptides. The vector is typically selected to be functional in the particular host cell employed (i.e., the vector is compatible with the host cell machinery such that amplification of the gene and/or expression of the gene can occur). A nucleic acid molecule encoding a beta secretase polypeptide may be amplified/expressed in prokaryotic, yeast, insect (baculovirus systems) and/or eukaryotic host cells. Selection of the host cell will depend in part on whether an beta secretase polypeptide is to be post-translationally modified (e.g., glycosylated and/or phosphorylated). If so, yeast, insect, or mammalian host cells are preferable.

Typically, expression vectors used in any of the host cells will contain sequences for plasmid maintenance and for cloning and expression of exogenous nucleotide sequences. Such sequences, collectively referred to as "flanking sequences" will typically include one or more of the following nucleic acid molecules: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag" sequence, i.e., an oligonucleotide molecule located at the 5' or 3' end of the beta secretase polypeptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the beta secretase polypeptide from the host cell. Affinity purification can be accomplished, for example, by column chromatography using antibodies against the tag as an affinity matrix. Optionally, the tag can subsequently be removed from the purified beta secretase polypeptide by various means such as using one or more selected peptidases for cleavage.

Flanking sequences may be homologous (i.e., from the same species and/or strain as the host cell), heterologous (i.e., from a species other than the host cell species or strain), hybrids (i.e., a combination of flanking sequences from more than one source), or synthetic, or native sequences which normally function to regulate beta secretase expression. As such, the source of flanking sequences may be any prokaryotic or eukaryotic organism, any vertebrate or invertebrate organism, or any plant, provided that the flanking sequence is(are) functional in, and can be activated by, the host cell machinery.

The flanking sequences useful in the vectors of this invention may be obtained by any of several methods well known in the art. Typically, flanking sequences useful herein other than the beta secretase gene flanking sequences will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described above for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography, or other method known to the skilled artisan. Selection of suitable enzymes to accomplish this purpose will be readily apparent to one of ordinary skill in the art.

An origin of replication is typically a part of prokaryotic expression vectors purchased commercially, and aids in the amplification of the vector in a host cell. Amplification of the vector to a certain copy number can, in some cases, be important for optimal expression of the beta secretase polypeptide. If the vector of choice does not contain an origin of replication site, one may be chemically synthesized based on a known sequence, and ligated into the vector.

The origin of replication from the plasmid pBR322 (Product No. 303-3S, New England Biolabs, Beverly, Mass.) is suitable for most Gram-negative bacteria. Various origin of replication elements (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes beta secretase. As a result, increased quantities of beta secretase are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the beta secretase polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A leader, or signal, sequence may be used to direct an beta secretase polypeptide out of the host cell. Typically, the signal sequence is positioned in the coding region of the beta secretase nucleic acid molecule, or directly at the 5' end of the beta secretase polypeptide coding region.

The signal sequence may be a component of the vector, or it may be a part of beta secretase DNA that is inserted into the vector. The native beta secretase DNA encodes a signal sequence at the amino terminus of the protein that is cleaved during post-translational processing of the molecule to form the mature beta secretase protein product.

Included within the scope of this invention are beta secretase nucleic acid molecules with the native signal sequence as well as beta secretase nucleic acid molecules wherein the native signal sequence is deleted and replaced with a heterologous signal sequence. The heterologous signal sequence selected should be one that is recognized and processed, i.e., cleaved by a signal peptidase, by the host cell. For expression of beta secretase in prokaryotic host cells, the native signal sequence is typically replace by a prokaryotic signal sequence selected, for example, from the group of the alkaline phosphatase, penicillinase, or heat-stable enterotoxin II leaders. For beta secretase expression in yeast host cells, the native beta secretase signal sequence may be substituted by any of the yeast invertase, alpha factor, or acid phosphatase signal sequences. For beta secretase expression in mammalian host cells, the native beta secretase signal sequence is satisfactory, although other mammalian signal sequences may be suitable.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the beta secretase gene, especially where the gene used is a full length genomic sequence or a fragment thereof. Where the intron is not naturally occurring within the gene (as for most cDNAs), the intron(s) may be obtained from another source. The position of the intron with respect to flanking sequences and the beta secretase gene is generally important, as the intron must be transcribed to be effective. Thus, when an beta secretase cDNA molecule is being expressed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will typically contain a promoter that is recognized by the host organism and operably linked to the molecule encoding the beta secretase polypeptide. Promoters are untranslated nucleic acid molecules located upstream (5') to the start codon of a structural gene (generally within about 100 to 1000 bp) that control the transcription and translation of a particular molecule, such as the beta secretase gene. Promoters are conventionally grouped into one of two classes, inducible promoters and constitutive promoters. Inducible promoters initiate increased levels of transcription of the structural gene in response to some change in culture conditions, such as the presence or absence of a nutrient or a change in temperature.

A large number of promoters that are functional in various host cells are well known and readily available. These promoters can be operably linked to the DNA encoding beta secretase by removing the native promoter from the beta secretase gene (via restriction enzyme digestion) and inserting the desired promoter into the vector. While the native beta secretase promoter sequence may be used to direct amplification and/or expression of the beta secretase gene in mammalian cells, a heterologous promoter is preferred if it permits greater transcription and higher yields of beta secretase polypeptide as compared to the native beta secretase promoter, and if it is compatible with the host cell system that has been selected for use.

Promoters suitable for use with prokaryotic hosts include, without limitation, the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any required restriction sites.

Suitable promoter sequences for use with yeast host cells are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40).

Suitable mammalian host cell promoters include heterologous mammalian promoters, e.g., heat-shock promoters and the actin promoter.

Additional promoters which may be of interest in controlling beta secretase expression include, but are not limited to: the SV40 early promoter region; the CMV promoter; the promoter contained in the 3' long terminal repeat of Rous sarcoma virus; the herpes thymidine kinase promoter; the regulatory sequences of the metallothionine gene; prokaryotic expression vectors such as the beta-lactamase promoter; or the tac promoter. Also of interest are the following animal transcriptional control regions, which exhibit tissue specificity and have been utilized in transgenic animals: the insulin gene control region which is active in pancreatic beta cells; the immunoglobulin gene control region which is active in lymphoid cells; the mouse mammary tumor virus control region which is active in testicular, breast, lymphoid and mast cells; albumin gene control region which is active in liver; the alphafetoprotein gene control region which is active in liver; the alpha 1-antitrypsin gene control region which is active in the liver; the beta-globin gene control region which is active in myeloid cells; the myelin basic protein gene control region which is active in oligodendrocyte cells in the brain; the myosin light chain-2 gene control region which is active in skeletal muscle; and the gonadotropic releasing hormone gene control region which is active in the hypothalamus.

Another optional component of the vector used for beta secretase polypeptide expression is the enhancer element. This nucleic acid molecule may be inserted into the vector to increase the transcription in higher eukaryotic host cells of a genomic DNA or cDNA molecule encoding beta secretase polypeptide. Enhancers are usually about 10-300 nucleotides in length and act on the promoter to increase its transcription. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancers useful for the activation of eukaryotic promoters. While an enhancer may be inserted into the vector either 5' or 3' to the beta secretase gene or cDNA, it is typically located at a site 5' from the promoter.

Expression vectors of the invention may be constructed from a starting vector such as a commercially available vector. Such vectors may or may not contain all of the desired flanking sequences. Where one or more of the flanking sequences set forth above are not already present in the vector to be used, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, PCRII, pCR3, and pcDNA3.1 (Invitrogen Company, San Diego, Calif.), pBSII (Stratagene Company, La Jolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

Additional possible vectors include, but are not limited to, cosmids, plasmids or modified viruses, but the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

After the vector has been constructed and a nucleic acid molecule encoding an beta secretase polypeptide has been inserted into the proper site of the vector, the completed vector may be inserted into a suitable host cell for amplification and/or polypeptide expression.

Host cells may be prokaryotic host cells (such as E. coli) or eukaryotic host cells (such as a yeast cell, an insect cell, or a vertebrate cell). The host cell, when cultured under appropriate conditions, synthesizes an beta secretase polypeptide which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are necessary for activity, such as glycosylation or phosphorylation, and ease of folding into a biologically active molecule.

Suitable host cells or cell lines may be mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5a, DH10, and MC1061 are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *Saccharomyces cerivisae*.

Additionally, where desired, insect cell systems may be utilized in the methods of the present invention. Such systems are described for example in Kitts et al. (*Biotechniques*, 14:810-817 [1993]), Lucklow (*Curr. Opin. Biotechnol.*, 4:564-572 [1993]) and Lucklow et al. (*J. Virol.*, 67:4566-4579 [1993]). Preferred insect cells are Sf-9 and Hi5 (Invitrogen, Carlsbad, Calif.).

Transformation or transfection of an expression vector for an beta secretase polypeptide into a selected host cell may be accomplished by well known methods including methods such as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

Polypeptide Production

Host cells comprising a beta secretase expression vector may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of a beta secretase polypeptide produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If a beta secretase polypeptide has been designed to be secreted from the host cells, the majority of polypeptide may be found in the cell culture medium. If however, the beta secretase polypeptide is not secreted from the host cells, it will be present in the cytoplasm and/or the nucleus (for eukaryotic host cells) or in the cytosol (for gram negative bacteria host cells).

For a beta secretase polypeptide situated in the host cell cytoplasm and/or nucleus, the host cells are typically first disrupted mechanically or with detergent to release the intracellular contents into a buffered solution. Beta secretase polypeptide can then be isolated from this solution.

Purification of a beta secretase polypeptide from solution can be accomplished using a variety of techniques. If the polypeptide has been synthesized such that it contains a tag such as hexahistidine or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing beta secretase polypeptide). For example, polyhistidine binds with great affinity and specificity to nickel, thus an affinity column of nickel (such as the Qiagen® nickel columns) can be used for purification of beta secretase polypeptide/poly-His. (See for example, Ausubel et al., eds., *Current Protocols in Molecular Biology*, Section 10.11.8, John Wiley & Sons, New York [1993]).

Where a beta secretase polypeptide is prepared without a tag attached and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If a beta secretase polypeptide is produced intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a beta secretase polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The beta secretase polypeptide in its now soluble form can then be analyzed using gel electrophoresis, immunoprecipitation or the like. If it is desired to isolate the beta secretase polypeptide, isolation may be accomplished using standard methods such as those set forth below and in Marston et al. (*Meth. Enz.*, 182:264-275 [1990]).

In some cases, a beta secretase polypeptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotropic agent. In most cases the refolding/oxidation solution will also contain a reducing agent or a reducing agent plus its oxidized form in a specific ratio to generate a particular redox potential allowing for disulfide shuffling to occur in the formation of cysteine bridge(s) of the polypeptide. Some commonly used redox couples include cysteine/cystamine, glutathione (GSH)/dithiobis GSH, cupric chloride, dithiothreitol (DTT)/dithiane DTT, 2-mercaptoethanol (bME)/dithio-b (ME). In many instances a cosolvent is necessary to increase the efficiency of the refolding and the more common reagents used for this purpose include glycerol, polyethylene glycol of various molecular weights, arginine and the like.

If inclusion bodies are not formed to a significant degree upon expression of an beta secretase polypeptide, the polypeptide will be found primarily in the supernatant after centrifugation of the cell homogenate and may be further isolated from the supernatant using methods such as those set forth below.

In situations where it is preferable to partially or completely purify an beta secretase polypeptide such that it is partially or substantially free of contaminants, standard methods known to the one skilled in the art may be used. Such methods include, without limitation, separation by electrophoresis followed by electroelution, various types of chromatography (affinity, immunoaffinity, molecular sieve, and/or ion exchange), and/or high pressure liquid chromatography. In some cases, it may be preferable to use more than one of these methods for complete purification.

Beta secretase polypeptides, fragments, and/or derivatives thereof may also be prepared by chemical synthesis methods using techniques known in the art such as those set forth by Merrifield et al., (*J. Am. Chem. Soc.*, 85:2149 [1963]), Houghten et al. (*Proc Natl Acad. Sci. USA*, 82:5132 [1985]), and Stewart and Young (*Solid Phase Peptide Synthesis*, Pierce Chemical Co., Rockford, Ill. [1984]). Using these methods, beta secretase fragments of up to about 75 amino acids in length can be prepared.

Typically, beta-secretase fragments and variants are synthesized from readily available starting materials. Synthesis is usually conducted from carboxy to amino terminus. During synthesis, the alpha-amine of the amino acid to be added is protected by a urethane such as Boc, Cbz, Fmoc, or Alloc (see Greene et al., *Protective Groups in Organic Synthesis*, 2d. ed., John Wiley and Sons [1991] for a list of protective groups) while the free carboxyl is activated with an activating reagent which is usually a carbodiimide such as DCC (Dicyclohexyl carbodiimide), EDC (1-(3-dimethylaminopropyl)-3-ethyl-carbodiimide), or DIC (diisopropylcarbodiimide). A preferred protective group is Fmoc. The activating reagent can optionally be used in the presence of a catalyst such as Hobt (N-Hydroxybenzotriazole) Hoat (7-aza-N-hydroxybenzotriazole), Hosu, or Dmap (Dimethylaminopyridine). After the peptide is completely synthesized, the side chain protecting groups may be removed using methods set forth in the above cited references. Such methods include, without limitation, hydrogenation in the presence of a catalyst such as palladium, platinum, or rhodium; treatment with sodium in liquid ammonia, hydrochloric, hydrofluoric, hydrobromic, formic, trifluoromethanesulfonic, or trifluoroacetic acid; secondary amines; fluoride ion; trimethylsilyl halides such as bromide and iodide; or alkali.

The above described methods may be accomplished manually or using an automated peptide synthesizer such as an Applied Biosystems model 430, 430A, A431, or A433, using programming modules as defined by the manufacturer's manuals.

To generate beta secretase fragments or variants using chemical synthesis that are longer than about 75 amino acids, a technique known as chemical ligation can be used in which peptides can be ligated together. This technique is described by Baca et al. (*J. Amer. Chem. Soc.*, 117:1881-1887 [1995]) and by Schnolver et al. (*Int. J. Peptide Protein Res.*, 40:180-193 [1992]).

Chemically synthesized beta-secretase polypeptides, fragments, and variants may be oxidized to permit the formation of disulfide bridges using standard methods set forth in the above cited references.

The beta-secretase polypeptides or fragments thereof are expected to have biological activity comparable to beta-secretase polypeptides or fragments thereof produced recombinantly and thus may be used interchangeably with recombinant or beta-secretase peptide.

Another means of obtaining beta secretase polypeptide is via purification from biological samples such as source tissues and/or fluids in which the beta secretase polypeptide is naturally found. Such purification can be conducted using methods for protein purification as described above. The presence of the beta secretase polypeptide during purification may be monitored using, for example, an antibody prepared against recombinantly produced beta secretase polypeptide or peptide fragments thereof.

Polypeptides

Polypeptides of the invention include isolated beta secretase polypeptides and polypeptides related thereto including fragments, variants, fusion polypeptides, and derivatives as defined hereinabove.

Beta secretase fragments of the invention may result from truncations at the amino terminus (with or without a leader sequence), truncations at the carboxy terminus, and/or deletions internal to the polypeptide. In preferred embodiments, truncations and/or deletions comprise about 10 amino acids, or about 20 amino acid, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such beta secretase polypeptides fragments may optionally comprise an amino terminal methionine residue.

Preferred beta secretase polypeptide fragments of SEQ ID NO: 4 include: amino acids 45-501; amino acids 46-501; amino acids 46-460; amino acids 45-460; amino acids 1-460; amino acids 93-292; amino acids 93-293; amino acids 91-295; amino acids 90-295; amino acids 90-300; amino acids 62-420; amino acids 1-420; amino acids 62-460; amino acids 90-460; amino acids 62-501; amino acids 62-460; amino acids 90-293; amino acids 90-300; amino acids 1-420; amino acids 46-420; amino acids 62-420; amino acids 73-420; amino acids 83-420; amino acids 90-420; amino acids 62-417; amino acids 73-417; amino acids 83-417; amino acids 90-417; amino acids 62-410; amino acids 73-410; amino acids 83-410; amino acids 90-410; amino acids 62-402; amino acids 73-402; amino acids 83-402; and amino acids 90-402.

Additionally preferred fragments include each of the foregoing prepared as a fusion peptide with a second peptide or polypeptide such as, for example, the Fc portion of human IgG.

Beta secretase polypeptide variants of the invention include one or more amino acid substitutions, additions and/or deletions as compared to any of SEQ ID NOS: 4, 5, and 6. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as defined above, or non-conservative or any combination thereof. The variants may have additions of amino acid residues either at the carboxy terminus or at the amino terminus (with or without a leader sequence).

Preferred beta secretase polypeptide variants include glycosylation variants wherein the number and/or type of glycosylation sites has been altered compared to native beta secretase polypeptide. In one embodiment, beta secretase variants comprise a greater or a lesser number of N-linked glycosylation sites. An N-linked glycosylation site is characterized by the sequence: Asn-X-Ser or Thr, where the amino acid residue designated as X may be any type of amino acid except proline. Substitution(s) of amino acid residues to create this sequence provides a potential new site for addition of an N-linked carbohydrate chain. Alternatively, substitutions to eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Beta secretase fusion polypeptides of the invention comprise beta secretase polypeptides, fragments, variants, or derivatives fused to a heterologous peptide or protein. Heterologous peptides and proteins include, but are not limited to, an epitope to allow for detection and/or isolation of an beta secretase fusion polypeptide, a transmembrane receptor protein or a portion thereof, such as an extracellular domain, or a transmembrane and intracellular domain, a ligand or a portion thereof which binds to a transmembrane receptor protein, an enzyme or portion thereof which is catalytically active, a protein or peptide which promotes oligomerization, such as leucine zipper domain, and a protein or peptide which increase stability, such as an immunoglobulin constant region. An beta secretase polypeptide may be fused to itself or to a fragment, variant, or derivative thereof. Fusions may be made either at the amino terminus or at the carboxy terminus of an beta secretase polypeptide, and may be direct with no linker or adapter molecule or may be through a linker or adapter molecule, such as one or more amino acid residues up to about 20 amino acids residues, or up to about 50 amino acid residues. A linker or adapter molecule may also be designed with a cleavage site for a DNA restriction endonuclease or for a protease to allow for separation of the fused moieties.

In a preferred embodiment, a beta secretase polypeptide, fragment, variant and/or derivative is fused to an Fc region of human IgG. In one example, a human IgG hinge, CH2 and CH3 region may be fused at either the N-terminus or C-terminus of the beta secretase polypeptides using methods known to the skilled artisan. In another example, a portion of a hinge regions and CH2 and CH3 regions may be fused. The beta secretase Fc-fusion polypeptide so produced may be purified by use of a Protein A affinity column. In addition, peptides and proteins fused to an Fc region have been found to exhibit a substantially greater half-life in vivo than the unfused counterpart. Also, a fusion to an Fc region allows for dimerization/multimerization of the fusion polypeptide.

Beta secretase polypeptide derivatives are included in the scope of the present invention. Such derivatives are chemically modified beta secretase polypeptide compositions in which beta secretase polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of beta secretase polypeptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and poly-vinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1-C10 alkoxy or aryloxy derivatives thereof (see U.S. Pat. No. 5,252,714).

Pegylation of beta secretase polypeptides may be carried out by any of the pegylation reactions known in the art, as described for example in the following references: *Focus on Growth Factors* 3: 4-10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable conditions used to react a biologically active substance with an activated polymer molecule. Methods for preparing pegylated beta secretase polypeptides will generally comprise the steps of (a) reacting the polypeptide with polyethylene glycol (such as a reactive ester or aldehyde derivative of PEG) under conditions whereby beta secretase polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product.

In a preferred embodiment, the beta secretase polypeptide derivative will have a single PEG moiety at the N terminus.

Generally, conditions which may be alleviated or modulated by administration of the present beta secretase polypeptide derivative include those described herein for beta secretase polypeptides. However, the beta secretase polypeptide derivative disclosed herein may have additional activities enhanced or reduced biological activity, or other characteristics, such as increased or decreased half-life, as compared to the non-derivatized molecules.

Antibodies

Beta secretase polypeptides, fragments, variants and derivatives may be used to prepare antibodies using methods known in the art. Thus, antibodies and antibody fragments that bind beta secretase polypeptides are within the scope of the present invention. Antibodies may be polyclonal, monoclonal, recombinant, chimeric, humanized, fully human, single chain and/or bispecific.

Polyclonal antibodies directed toward a beta secretase polypeptide generally are raised in animals (rabbits or mice) by multiple subcutaneous or intraperitoneal injections of beta secretase in combination with an adjuvant. It may be useful to conjugate a beta secretase polypeptide, or a variant, fragment or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals can be bled and the serum is assayed for anti-beta secretase antibody titer.

Monoclonal antibodies directed toward beta secretase polypeptide can be produced using any method which provides for the production of antibody molecules by continuous cell lines in culture. Examples of suitable methods for preparing monoclonal antibodies include hybridoma method of Kohler et al., *Nature* 256: 495-497 (1975), and the human B-cell hybridoma method, Kozbor, *J. Immunol.* 133: 3001 (1984); Brodeur et al., *Monoclonal Antibody Production Techniques and Applications*, pp. 51-63 (Marcel Dekker, Inc., New York, 1987).

Also provided by the invention are hybridoma cell lines which produce monoclonal antibodies reactive with beta secretase polypeptides.

Monoclonal antibodies of the invention may be modified for use as therapeutics. One embodiment is a "chimeric" antibody in which a portion of the heavy and/or light chain is identical with or homologous to corresponding sequence in antibodies derived from a particular species or belonging to a particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci.* 81, 6851-6855 [1985]).

Also included in the scope of the present invention are monoclonal antibodies that are "humanized". Methods for humanizing non-human antibodies are well known in the art. Humanization can be performed following methods known in the art (see Jones et al., *Nature* 321: 522-525 [1986]; Riechmann et al., *Nature,* 332: 323-327 [1988]; Verhoeyen et al., *Science* 239: 1534-1536 [1988]), by substituting rodent complementarily-determining regions (CDRs) for the corresponding regions of a human antibody.

Also encompassed by the invention are fully human antibodies which bind beta secretase polypeptides, fragments, variants and/or derivatives. Such antibodies can be produced by immunization with an beta secretase antigen (optionally conjugated to a carrier) of transgenic animals (e.g., mice) that are capable of producing a repertoire of human antibodies in the absence of endogenous immunoglobulin production. See, for example, Jakobovits et al., *Proc. Natl. Acad. Sci.* 90: 2551-2555 (1993); Jakobovits et al., *Nature* 362: 255-258 (1993); Bruggermann et al., *Year in Immuno.* 7:33 (1993).

Human antibodies can also be produced in phage-display libraries (see Hoogenboom et al., *J. Mol. Biol.* 227:381 [1991]; Marks et al., *J. Mol. Biol.* 222:581 [1991]).

For diagnostic applications, anti-beta secretase antibodies typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, β-galactosidase or horseradish peroxidase.

The anti-beta secretase antibodies of the invention may be employed in any known assay method, such as competitive binding assays, direct and indirect sandwich assays, and immunoprecipitation assays (see Sola, *Monoclonal Antibodies: A Manual of Techniques*, pp. 147-158 [CRC Press, Inc., 1987]) for detection and quantitation of beta secretase polypeptides. The antibodies will bind beta secretase polypeptides with an affinity which is appropriate for the assay method being employed.

Competitive binding assays rely on the ability of a labeled standard (e.g., an beta secretase polypeptide, or an immunologically reactive portion thereof) to compete with the test sample analyte (an beta secretase polypeptide) for binding with a limited amount of anti beta secretase antibody. The amount of an beta secretase polypeptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See U.S. Pat. No. 4,376, 110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

The anti-beta secretase antibodies of the invention also are useful for in vivo imaging, wherein an antibody labeled with a detectable moiety is administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Antibodies of the invention may be used as therapeutics. Therapeutic antibodies are generally agonists or antagonists, in that they either enhance or reduce, respectively, at least one of the biological activities of an beta secretase polypeptide. Antagonist antibodies of the invention are antibodies or binding fragments thereof which are capable of specifically binding to an beta secretase polypeptide, fragment, variant and/or derivative, and which are capable of inhibiting or eliminating the functional activity of an beta secretase polypeptide in vivo or in vitro. In preferred embodiments, an antagonist antibody will inhibit the functional activity of an beta secretase polypeptide at least about 50 percent, and preferably at least about 80 percent. Agonist and antagonist anti-beta secretase antibodies are identified by screening assays described below.

Genetically Engineered Non-Human Mammals

Included within the scope of the present invention are non-human mammals such as mice, rats, rabbits, goats, or sheep in which one or both alleles of the gene encoding a native beta secretase polypeptide has (have) been disrupted ("knocked out") such that the level of expression of this gene is decreased or completely abolished. Such mammals may be prepared using techniques and methods such as those described in U.S. Pat. No. 5,557,032. Such beta secretase knockout mammals have use in evaluating the effects of decreased beta secretase expression on Alzheimer's disease.

The present invention further includes non-human mammals such as mice, rats, rabbits, goats, or sheep in which the gene (or genes) encoding beta secretase polypeptides in which either the native form of the gene(s) for that mammal or a heterologous beta secretase polypeptide gene(s) is (are) over-expressed by the mammal, thereby creating a "transgenic" mammal. Such transgenic mammals may be prepared using well known methods such as those described in U.S. Pat. No. 5,489,743 and PCT Publication No. WO94/28122. Such transgenic mammals have use in evaluating the effects of over production of beta secretase on Alzheimer's disease.

The present invention further includes non-human mammals in which the promoter for one or more of the beta secretase polypeptides of the present invention is either activated or inactivated (using homologous recombination methods as described below) to alter the level of expression of one or more of the native beta secretase polypeptides. These mammals have uses similar to those set forth for transgenic and knockout mammals.

Modulators of Beta Secretase Polypeptide Activity

In some situations, it may be desirable to identify molecules that are modulators, i.e., agonists or antagonists, of the activity of beta secretase polypeptide.

Natural or synthetic molecules that modulate beta secretase can be identified using one or more of the screening assays described below. Such molecules may be administered either in an ex vivo manner, or in an in vivo manner by local or IV injection, or by oral delivery, implantation device, or the like.

The following definition is used herein for describing the assays:

"Test molecule(s)" refers to the molecule(s) that is/are under evaluation for the ability to modulate beta secretase polypeptide activity. Such test molecule may be an agonist or antagonist of beta secretase.

Methods for identifying compounds which modulate beta secretase activity are encompassed by the present invention. In general, a beta secretase polypeptide can be incubated with a test molecule under conditions which permit the interaction of the test molecule with beta secretase polypeptide, and the extent of the interaction can then be measured. The test molecule may be screened in a substantially purified form or in a crude mixture. Test molecules may be nucleic acid molecules, proteins, peptides, carbohydrates, lipids or small molecular weight organic or inorganic compounds. Once a set of test molecules has been identified as binding to an beta secretase polypeptide, the molecules may be further evaluated for their ability to increase or decrease beta secretase activity.

Measurement of the interaction of test molecules with beta secretase polypeptides may be carried out in several formats, including, without limitation, enzymatic assays, cell-based assays, solution-phase assays, immunoassays, and in vivo assays. In general, test molecules are incubated with an beta secretase polypeptide for a specified period of time and the extent of beta secretase activity can then be determined by the biological activity assay set forth herein, or by other appropriate assays such as immunoassays.

The beta secretase agonist or antagonist may be a protein, peptide, carbohydrate, lipid or small molecular weight molecule which interacts with beta secretase to regulate its activity. Potential protein antagonists of beta secretase include antibodies which bind to active regions of the polypeptide and inhibit or eliminate at least once activity of beta secretase. Molecules which regulate beta secretase polypeptide expression may include nucleic acids which are complementary to nucleic acids encoding an beta secretase polypeptide, or are complementary to nucleic acids sequences which direct or control expression of beta secretase polypeptide, and which act as anti-sense regulators of expression.

In some cases, it may be desirable to evaluate two or more test compounds together for their ability to modulate beta secretase polypeptide activity. In these cases, the assays can be readily modified by adding such additional test compound(s) either simultaneous with, or subsequent to, the first test compound.

In vitro assays such as the biological activity assay described herein may be used advantageously to rapidly screen large numbers of compounds for effects on the activity of beta secretase. The assays may be automated to screen compounds generated using phage display, synthetic peptide and chemical synthesis libraries.

Compounds which increase or decrease beta secretase activity may be screened in cell culture using cells and cell lines expressing beta secretase. Cells and cell lines may be obtained from any mammal, but preferably will be from human or other primate, canine, or rodent sources.

Beta Secretase Compositions and Administration

Therapeutic compositions of beta secretase polypeptides are within the scope of the present invention. Such compositions may comprise a therapeutically effective amount of a beta secretase polypeptide, fragment, variant, or derivative in admixture with a pharmaceutically acceptable agent such as a pharmaceutically acceptable carrier. The carrier material may be water for injection, preferably supplemented with other materials common in solutions for administration to mammals. Typically, a beta secretase polypeptide therapeutic compound will be administered in the form of a composition comprising purified polypeptide, fragment, variant, or derivative in conjunction with one or more physiologically acceptable agents. Neutral buffered saline or saline mixed with serum albumin are exemplary appropriate carriers. Preferably, the product is formulated as a lyophilizate using appropriate excipients (e.g., sucrose). Other standard pharmaceutically acceptable agents such as carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

Beta secretase pharmaceutical compositions typically include a therapeutically or prophylactically effective amount of beta secretase protein in admixture with one or more pharmaceutically and physiologically acceptable formulation agents selected for suitability with the mode of administration. Suitable formulation materials or pharmaceutically acceptable agents include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to a formulation agent(s) suitable for accomplishing or enhancing the delivery of the beta secretase protein as a pharmaceutical composition.

The primary solvent in a composition may be either aqueous or non-aqueous in nature. In addition, the vehicle may contain other formulation materials for modifying or maintaining the pH, osmolarity, viscosity, clarity, color, sterility, stability, rate of dissolution, or odor of the formulation. Similarly, the composition may contain additional formulation materials for modifying or maintaining the rate of release of beta secretase protein, or for promoting the absorption or penetration of beta secretase protein.

The beta secretase polypeptide compositions can be administered parentally. Alternatively, the compositions may be administered intravenously or subcutaneously. When systemically administered, the therapeutic compositions for use in this invention may be in the form of a pyrogen-free, parentally acceptable aqueous solution. The preparation of such pharmaceutically acceptable protein solutions, with due regard to pH, isotonicity, stability and the like, is within the skill of the art.

Therapeutic formulations of beta secretase polypeptide compositions useful for practicing the present invention may be prepared for storage by mixing the selected composition having the desired degree of purity with optional physiologically acceptable carriers, excipients, or stabilizers (*Remington's Pharmaceutical Sciences,* 18th Edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

The optimal pharmaceutical formulation will be determined by one skilled in the art depending upon the intended route of administration, delivery format and desired dosage. See for example, *Remington's Pharmaceutical Sciences,* 18th Ed. (1990, Mack Publishing Co., Easton, Pa. 18042 pages 1435-1712). Such compositions may influence the physical state, stability, rate of in vivo release, and rate of in vivo clearance of the present beta secretase protein.

An effective amount of an beta secretase polypeptide composition to be employed therapeutically will depend, for example, upon the therapeutic objectives such as the indication for which the beta secretase polypeptide is being used, the route of administration, and the condition of the patient. Accordingly, it may be necessary for the therapist to titer the dosage and modify the route of administration as required to obtain the optimal therapeutic effect. A typical daily dosage may range from about 0.1 µg/kg to up to 100 mg/kg or more, depending on the factors mentioned above. Typically, a clinician will administer the composition until a dosage is reached that achieves the desired effect. The composition may therefore be administered as a single dose, or as two or more doses (which may or may not contain the same amount of beta secretase polypeptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The beta secretase polypeptide composition to be used for in vivo parenteral administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

Effective administration forms, such as (1) slow-release formulations, (2) inhalant mists, or (3) orally active formulations are also envisioned. The beta secretase pharmaceutical composition also may be formulated for parenteral administration. Such parenterally administered therapeutic compositions are typically in the form of a pyrogen-free, parenterally acceptable aqueous solution comprising beta secretase in a pharmaceutically acceptable vehicle. The beta secretase pharmaceutical compositions also may include particulate preparations of polymeric compounds such as polylactic acid, polyglycolic acid, etc. or the introduction of beta secretase into liposomes. Hyaluronic acid may also be used, and this may have the effect of promoting sustained duration in the circulation.

A particularly suitable vehicle for parenteral injection is sterile distilled water in which beta secretase is formulated as a sterile, isotonic solution, properly preserved. Yet another preparation may involve the formulation of beta secretase with an agent, such as injectable microspheres, bio-erodible particles or beads, or liposomes, that provides for the controlled or sustained release of the protein product which may then be delivered as a depot injection. Other suitable means for the introduction of beta secretase include implantable drug delivery devices which contain the beta secretase.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

A pharmaceutical composition may be formulated for inhalation. For example, beta secretase may be formulated as a dry powder for inhalation. beta secretase inhalation solutions may also be formulated in a liquefied propellant for aerosol delivery. In yet another formulation, solutions may be nebulized.

It is also contemplated that certain formulations containing beta secretase may be administered orally. Beta secretase which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of beta secretase. Diluents, flavorings, low melting point waxes, vegetable oils, lubricants, suspending agents, tablet disintegrating agents, and binders may also be employed.

Another preparation may involve an effective quantity of beta secretase in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional beta secretase formulations will be evident to those skilled in the art, including formulations involving beta secretase in combination with one or more other therapeutic agents. Techniques for formulating a variety of other sustained- or controlled-delivery means, such as liposome carriers, bio-erodible microparticles or porous beads and depot injections, are also known to those skilled in the art. See, for example, the Supersaxo et al. description of controlled release porous polymeric microparticles for the delivery of pharmaceutical compositions (International Publication No. WO 93/15722; International Application No. PCT/US93/00829) the disclosure of which is hereby incorporated by reference.

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Alternatively or additionally, the composition may be administered locally via implantation into the affected area of a membrane, sponge, or other appropriate material on to which beta secretase polypeptide has been absorbed or encapsulated.

Where an implantation device is used, the device may be implanted into any suitable tissue or organ, and delivery of beta secretase polypeptide may be directly through the device via bolus, or via continuous administration, or via catheter using continuous infusion.

Beta secretase polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547-556 [1983]), poly(2-hydroxyethyl-methacrylate) (Langer et al., *J. Biomed. Mater. Res.,* 15: 167-277 [1981] and Langer, *Chem. Tech.,* 12: 98-105 [1982]), ethylene vinyl acetate (Langer et al., supra) or poly-D(−)-3-hydroxybutyric acid (EP 133,988). Sustained-release compositions also may include liposomes, which can be prepared by any of several methods known in the art (e.g., Eppstein et al., *Proc. Natl. Acad. Sci. USA,* 82: 3688-3692 [1985]; EP 36,676; EP 88,046; EP 143,949).

The beta secretase polypeptides, fragments thereof, variants, and derivatives, may be employed alone, together, or in combination with other pharmaceutical compositions. The beta secretase polypeptides, fragments, variants, and derivatives may be used in combination with other medicinal compounds such as, for example, cytokines, growth factors, antibiotics, anti-inflammatories, and/or chemotherapeutic agents as is appropriate for the indication being treated.

In some cases, it may be desirable to use beta secretase polypeptide compositions in an ex vivo manner. Here, cells, tissues, or organs that have been removed from the patient are exposed to beta secretase polypeptide compositions after which the cells, tissues and/or organs are subsequently implanted back into the patient.

In other cases, an beta secretase polypeptide may be delivered through implanting into patients certain cells that have been genetically engineered, using methods such as those described herein, to express and secrete the polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT WO 91/10425 (Aebischer et al.). The cells, with or without encapsulation, may be implanted into suitable body tissues or organs of the patient.

Gene Therapy and Homologous Recombination

Further included in the scope of the present invention is production of beta secretase polypeptide by homologous recombination, and production of beta secretase polypeptide using control elements introduced into cells containing beta secretase DNA. For example, homologous recombination methods may be used to modify a cell containing a transcriptionally active beta secretase gene to produce a cell which does not express therapeutically efficacious amounts of beta secretase.

Homologous recombination is a technique originally developed for targeting genes to induce or correct mutations in transcriptionally active genes (see Kucherlapati, *Prog. in Nucl. Acid Res. and Mol. Biol.*, 36:301, 1989). The basic technique was developed as a method for introducing specific mutations into specific regions of the mammalian genome (Thomas et al., *Cell*, 44:419-428, 1986; Thomas et al., *Cell*, 51:503-512, 1987; Doetschman et al., *Proc. Natl. Acad. Sci.*, 85:8583-8587, 1988) or to correct specific mutations within defective genes (Doetschman et al., *Nature*, 330:576-578, 1987). Exemplary homologous recombination techniques are described in U.S. Pat. No. 5,272,071 (EP 91 90 3051, EP Publication No. 505 500; and International Publication No. WO 91/09955).

Through homologous recombination, the DNA sequence to be inserted into the genome can be directed to a specific region of the gene of interest by attaching it to targeting DNA. The targeting DNA is a nucleic acid molecule that is complementary to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new DNA to serve as the template. Thus, this new DNA is incorporated into the genome.

Attached to these pieces of targeting DNA are regions of DNA which may interact with the expression of a beta secretase protein. For example, a promoter/enhancer element, a suppresser, or an exogenous transcription modulatory element is inserted in the genome of the intended host cell in proximity and orientation sufficient to influence the transcription of DNA encoding the desired beta secretase protein. The control element controls a portion of the DNA present in the host cell genome. Thus, the expression of beta secretase protein may be achieved not by transfection of DNA that encodes the beta secretase gene itself, but rather by the use of targeting DNA (containing regions of homology with the endogenous gene of interest) coupled with DNA regulatory segments that provide the endogenous gene sequence with recognizable signals for transcription of a beta secretase protein.

In an exemplary method, expression of a desired targeted gene in a cell (i.e., a desired endogenous cellular gene) can be altered by introducing an exogenous DNA molecule into a preselected site of genomic DNA. The exogenous DNA molecule typically includes at least a regulatory sequence, an exon and a splice donor site. This exogenous DNA is introduced into the genomic DNA in a location so as to produce a new transcription unit in which the regulatory sequence, the exon and the splice donor site present in the exogenous DNA are operatively linked to the endogenous gene. As a result of introduction of the exogenous DNA into the genomic DNA, the expression of the desired endogenous gene is altered.

Altered gene expression, as used herein, encompasses activating (or causing to be expressed) a gene which is normally silent (unexpressed) in the cell as obtained, increasing expression of a gene which is not expressed at physiologically significant levels in the cell as obtained, changing the pattern of regulation or induction such that it is different than occurs in the cell as obtained, and reducing (including eliminating) expression of a gene which is expressed in the cell as obtained.

The present invention further relates to DNA constructs useful in the method of altering expression of a target gene. Exemplary DNA constructs typically comprise the following components: (a) a targeting sequence; (b) a regulatory sequence; (c) an exon; and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of beta secretase presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA. The present invention, therefore, includes nucleotides encoding a beta secretase molecule, which nucleotides may be used as targeting sequences.

Cell based therapy via genetic manipulation is also included in the scope of the present invention. In those situations where it is desirable to increase the level of beta secretase activity in cells, beta secretase cell therapy, e.g., implantation of cells producing beta secretase, may be appropriate. This embodiment encompasses implanting into patients cells capable of synthesizing and secreting a biologically active form of beta secretase. Such beta secretase-producing cells may be cells that are natural producers of beta secretase or may be recombinant cells whose ability to produce beta secretase has been augmented by transformation with a gene encoding the desired beta secretase molecule or with a gene augmenting the expression of beta secretase. Such a modification may be accomplished by means of a vector suitable for delivering the gene as well as promoting its expression and secretion. In order to minimize a potential immunological reaction in patients being administered a beta secretase protein or polypeptide of a foreign species, it is preferred that the natural cells producing beta secretase be of human origin and produce human beta secretase. Likewise, it is preferred that the recombinant cells producing beta secretase be transformed with an expression vector containing a gene encoding a human beta secretase molecule.

Implanted cells may be encapsulated to avoid infiltration of surrounding tissue. Human or non-human animal cells may be implanted in patients in biocompatible, semipermeable polymeric enclosures or membranes that allow release of beta secretase, but that prevent destruction of the cells by the patient's immune system or by other detrimental factors from the surrounding tissue. Alternatively, the patient's own cells, transformed to produce beta secretase ex vivo, could be implanted directly into the patient without such encapsulation.

Techniques for the encapsulation of living cells are known in the art, and the preparation of the encapsulated cells and their implantation in patients may be accomplished without undue experimentation. For example, Baetge et al. (International Publication No. WO 95/05452) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538, 5,011,472, and 5,106,627. A system for encapsulating living cells is described in PCT Application WO 91/10425 of Aebischer et al. See also PCT Application WO 91/10470 of Aebischer et al.; Winn et al., *Exper. Neurol.*, 113:322-329, 1991; and Aebischer et al., *Exper. Neurol.*, 111:269-275, 1991.

In vivo and in vitro gene therapy delivery of beta secretase is also envisioned. In vivo gene therapy may be accomplished by introducing the gene encoding beta secretase into cells via local injection of a polynucleotide molecule or other appropriate delivery vectors. (Hefti, *J. Neurobiology*, 25:1418-1435, 1994). For example, a polynucleotide molecule encoding beta secretase may be contained in an adeno-associated virus vector for delivery to the targeted cells (e.g., Johnson, International Publication No. WO 95/34670; International Application No. PCT/US95/07178). The recombinant adeno-associated virus (AAV) genome typically contains AAV inverted terminal repeats flanking a DNA sequence encoding beta secretase operably linked to functional promoter and polyadenylation sequences.

Alternative viral vectors include, but are not limited to, retrovirus, adenovirus, herpes simplex virus and papilloma virus vectors. U.S. Pat. No. 5,672,344 (issued Sep. 30, 1997, Kelley et al., University of Michigan) describes an in vivo viral-mediated gene transfer system involving a recombinant neurotrophic HSV-1 vector. U.S. Pat. No. 5,399,346 (issued Mar. 21, 1995, Anderson et al., Department of Health and human Services) provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (issued May 20, 1997, Woo et al., Baylor College of Medicine) involving adenoviral vectors; U.S. Pat. No. 5,672,510 (issued Sep. 30, 1997, Eglitis et al., Genetic Therapy, Inc.) involving retroviral vectors; and U.S. Pat. No. 5,635,399 (issued Jun. 3, 1997, Kriegler et al., Chiron Corporation) involving retroviral vectors expressing cytokines.

Nonviral delivery methods include liposome-mediated transfer, naked DNA delivery (direct injection), receptor-mediated transfer (ligand-DNA complex), electroporation, calcium phosphate precipitation and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, transcription factors to enhance expression by a vector as well as methods of vector manufacture. Such additional methods and materials for the practice of gene therapy techniques are described in U.S. Pat. No. 4,970,154 (issued Nov. 13, 1990, D. C. Chang, Baylor College of Medicine) electroporation techniques; WO 9640958 (published 961219, Smith et al., Baylor College of Medicine) nuclear ligands; U.S. Pat. No. 5,679,559 (issued Oct. 21, 1997, Kim et al., University of Utah Research Foundation) concerning a lipoprotein-containing system for gene delivery; U.S. Pat. No. 5,676,954 (issued Oct. 14, 1997, K. L. Brigham, Vanderbilt University involving liposome carriers; U.S. Pat. No. 5,593,875 (issued Jan. 14, 1997, Wurm et al., Genentech, Inc.) concerning methods for calcium phosphate transfection; and U.S. Pat. No. 4,945,050 (issued Jul. 31, 1990, Sanford et al., Cornell Research Foundation) wherein biologically active particles are propelled at cells at a speed whereby the particles penetrate the surface of the cells and become incorporated into the interior of the cells. Expression control techniques include chemical induced regulation (e.g., WO 9641865 and WO 9731899), the use of a progesterone antagonist in a modified steroid hormone receptor system (e.g., U.S. Pat. No. 5,364,791), ecdysone control systems (e.g., WO 9637609), and positive tetracycline-controllable transactivators (e.g., U.S. Pat. Nos. 5,589,362; 5,650,298; and 5,654,168).

It is also contemplated that beta secretase gene therapy or cell therapy can further include the delivery of a second polypeptide. For example, the host cell may be modified to express and release both beta secretase and a second polypeptide of interest. Alternatively, the beta secretase and the second polypeptide of interest may be expressed in and released from separate cells. Such cells may be separately introduced into the patient or the cells may be contained in a single implantable device, such as the encapsulating membrane described above.

Gene therapy can be used to decrease beta secretase polypeptide expression by modifying the nucleotide sequence of the endogenous promoter(s). Such modification is typically accomplished via homologous recombination methods. For example, a DNA molecule containing all or a portion of the promoter of the beta secretase gene(s) selected for inactivation can be engineered to remove and/or replace pieces of the promoter that regulate transcription. Here, the TATA box and/or the binding site of a transcriptional activator of the promoter may be deleted using standard molecular biology techniques; such deletion can inhibit promoter activity thereby repressing transcription of the corresponding beta secretase gene. Deletion of the TATA box or transcription activator binding site in the promoter may be accomplished by generating a DNA construct comprising all or the relevant portion of the beta secretase polypeptide promoter(s) (from the same or a related species as the beta secretase gene(s) to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive.

This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' DNA sequences in the promoter construct can serve to help integrate the modified promoter region via hybridization to the endogenous chromosomal DNA.

Other gene therapy methods may also be employed where it is desirable to inhibit the activity of one or more beta secretase polypeptides. For example, antisense DNA or RNA molecules, which have a sequence that is complementary to at least a portion of the selected beta secretase polypeptide gene(s) can be introduced into the cell. Typically, each such antisense molecule will be complementary to the start site (5' end) of each selected beta secretase gene. When the antisense molecule then hybridizes to the corresponding beta secretase mRNA, translation of this mRNA is prevented.

Alternatively, gene therapy may be employed to create a dominant-negative inhibitor of one or more beta secretase polypeptides. In this situation, the DNA encoding a mutant full length or truncated polypeptide of each selected beta secretase polypeptide can be prepared and introduced into the cells of a patient using either viral or non-viral methods as described above. Each such mutant is typically designed to compete with endogenous polypeptide in its biological role.

Utility

Nucleic acid molecules of the invention may be used to map the locations of the beta secretase gene and related genes on chromosomes. Mapping may be done by techniques known in the art, such as PCR amplification and in situ hybridization.

In addition, the nucleic acid molecules can be used as anti-sense inhibitors of beta secretase expression. Such inhibition may be effected by nucleic acid molecules which are complementary to and hybridize to expression control sequences (triple helix formation) or to beta secretase mRNA. Anti-sense probes may be designed by available techniques using the sequence of beta secretase disclosed herein. Anti-sense inhibitors provide information relating to the decrease or absence of an beta secretase polypeptide in a cell or organism.

Hybridization probes may be prepared using the beta secretase nucleic acid molecules provided herein to screen cDNA, genomic or synthetic DNA libraries for related sequences. Regions of the DNA and/or amino acid sequence of beta secretase that exhibit significant identity to known sequences are readily determined using sequence alignment algorithms disclosed above and those regions may be used to design probes for screening.

Further, the nucleic acid molecules of the invention may be used for gene therapy. Nucleic acid molecules which express beta secretase in vivo provide information relating to the effects of the polypeptide in cells or organisms.

Beta secretase nucleic acid molecules, fragments, and/or derivatives that do not themselves encode biologically active polypeptides may be useful as hybridization probes in diagnostic assays to test, either qualitatively or quantitatively, for the presence of beta secretase DNA or corresponding RNA in mammalian tissue or bodily fluid samples.

Beta secretase polypeptide fragments, variants, and/or derivatives, whether biologically active or not, are useful for preparing antibodies that bind to a beta secretase polypeptide.

The antibodies may be used for in vivo and in vitro diagnostic purposes, such as in labeled form to detect the presence of beta secretase polypeptide in a body fluid or cell sample. Diagnosis of conditions such as Alzheimer's disease, Down's syndrome, and amyloid angiopathy may be accomplished by measuring beta-secretase levels and activity from bodily tissue or cell samples such as plasma, and comparing this data against known "normal" standards for each such condition. Beta-secretase levels can be measured by ELISA or Western blot for example; beta-secretase activity can be measured by the assays set forth in the Examples below. Abnormal results of one or both assays could indicate that a person is at high risk of developing such diseases, and early treatment could be started via administration of a beta-secretase inhibitor, for example.

Based on Northern blot data presented in the Examples below, beta-secretase expression is relatively high in the pancreas. This suggests that beta-secretase may be implicated in diseases such as acute and/or chronic pancreatitis, pancreatic cancer, and pancreobiliary duct obstruction, and modulation of the activity of beta-secretase may decrease the extent of, or completely prevent, such disorders.

The beta-secretase antibodies may bind to a beta-secretase polypeptide so as to diminish or block at least one activity characteristic of beta secretase polypeptide, or may bind to a beta-secretase polypeptide to increase its activity.

A plasmid containing cDNA encoding full length beta secretase has been transformed into in *E. coli* cells, and the cells have been deposited with the American Type Culture Collection, 10801 University Boulevard, Manassas, Va. 20110-2209 on Mar. 11, 1999. The cells have been designated as accession no. 207159.

A plasmid containing cDNA encoding amino acids 1-460 of beta-secretase fused to the Fc portion of human IgG beta has been transformed into in *E. coli* cells, and the cells have been deposited with the American Type Culture Collection, 10801 University Boulevard, Manassas, Va. 20110-2209 on Mar. 11, 1999. The cells have been designated as accession no. 207158.

The following examples are intended for illustration purposes only, and should not be construed as limiting the scope of the invention in any way.

EXAMPLE I

Production of an APP Expressing Cell Line

The human APP-695 cDNA containing the Swedish mutation (referred to as "APPΔNL" the sequence of which has been published Mullan et al., *Nature Genetics* 1: 345-347 [1992]) was digested with the restriction enzymes HindIII and NotI, and the approximately 2.6 kb HindIII-Not fragment was inserted into the vector pCMVi (Cell & Molecular Technologies Inc; Lavallette, N.J.) to generate the vector pCMVi-APPΔNL).

Human embryonic kidney 293 cells containing the SV40 large T antigen (Cell & Molecular Technologies, Lavallette, N.J.) were maintained in high glucose Dulbecco's modified Eagle's medium supplemented with about 10 percent fetal calf serum. At approximately 70 percent confluence the cells were co-transfected with pCMVi-APPΔNL and pRSV-Puro (Cell & Molecular Technologies Inc; Lavallette, N.J.) using the standard calcium phosphate method (Gorman et al, *DNA Prot. Eng. Tech.* 2: 3-10 [1990]). After about forty eight hours, puromycin resistant colonies were selected by adding puromycin (Sigma Inc., St. Louis, Mo.) at about 5 micrograms/ml to the culture medium. Fourteen days later, individual resistant colonies were isolated, using a pipetteman P200 (Rainin, Emeryville, Calif.) expanded into a 24 well dish and allowed to grow confluent. The conditioned media were analyzed for the presence of secreted APP by Western dot blot using the monoclonal antibody 22C11 (Boehringer Manheim Corp., Indianapolis, Ind.).

One colony was grown up and a cell line referred to as "293T-APPsw101" was generated from it.

EXAMPLE II

Construction of a Human Embryonic Kidney Cell Expression Library

Approximately $10^8$ 293 human embryonic kidney cells (ATCC CRL-1573), which are known to express the beta secretase gene, were grown to about 80 percent confluency in DMEM high glucose media supplemented with about 10 percent fetal bovine serum using T225 tissue culture flasks (Corning/Costar, Encinitas, Calif.). Cells were harvested in about 3 ml of 0.5 mM EDTA in PBS and pelleted at about 1100 RPM in a Beckman table top centrifuge. The cells were washed twice with cold PBS and snap frozen in liquid nitrogen as a dry cell pellet. Poly A+ mRNA was harvested from the cell pellet using the FastTrack™ method of mRNA isolation (Invitrogen, San Diego Calif.) according to the manufacturer's protocol. An oligo dT primed, directional cDNA expression library was prepared from about three µg of this poly A+ mRNA using the Superscript™ plasmid system for cDNA synthesis (Gibco BRL, Gaithersburg, Md.) according to the manufacturer's protocol. Sal I adaptors were ligated to the double stranded cDNA following the manufacturer's instructions.

After adaptor ligation, the cDNA was digested to completion with Not I, and size fractionated as per the manufacturer's protocol by column chromatography over a Sephacryl™ S-500 column which excludes cDNAs of 500 bp and smaller (provided by the manufacturer). Column fractions were counted on a Beckman scintillation counter and Cherenkov counts were obtained for each fraction. cDNAs from fractions 10-12 were ethanol precipitated and resuspended in about 22 microliters of nuclease free water. The cDNA products which averaged about 2.0 kb in length were directionally ligated into a CMV based expression vector (comparable to pRK-5; Pharmingen Inc., San Diego, Calif.) which had been previously digested with NotI and SalI. The ligated cDNA was then introduced into electrocompetent ElectroMax™ DH10B E. coli cells (Gibco BRL, Gaithersburg. MD) using standard electroporation procedures. The cDNA library was titered by serial dilution of the transformation cell mixture.

The cDNA library was subdivided into pools of 100, plated on LB agar plates containing about 100 micrograms/ml Ampicillin, and allowed to grow for about twenty hours. Cell colonies from each independent plate were then harvested in about two ml of 2×YT media, transferred to deep-well 96 well dishes and allowed to grow for an additional five to six hours at 37° C. The cells were pelleted by centrifugation at 3000 RPM in a Beckman table top centrifuge and DNA was prepared using the TurboPrep™ method of DNA isolation (Qiagen Inc., Chatsworth, Calif.) according to the manufacturer's protocol. DNA from each pool was arrayed in 96 well Corning Costar UV plates (CORNING Costar, Charlotte, N.C.) and quantitated by O.D. 260 using a Molecular Devices Spectra Max plus (Molecular Dynamics, Sunnyvale, Calif.).

A duplicate of each master cDNA 96 well plate was prepared. Each well of the duplicate plate contained about 75 microliters of Optimem I medium (Life Technologies Inc, Gaithersburg, Md.) and about 300 ng of cDNA library. About 75 microliters of a mixture of 12 microliters DMRIE-C Lipid per ml of Optimem I medium (Life Technologies Inc., Gaithersburg, Md.) was added to each well of the 96 well plate using a Multipette (Sagian Inc. Indianapolis, Ind.) robotic pipettor. The DMRIE C was allowed to complex for about 30 minutes. Meanwhile, the media was removed from a 96 well dish in which each well had been plated with about 15,000 cells/well of the 293T-APPsw 101 cell line two days before. About 125 microliters of the DNA/Lipid complex was added to each well of cells. The cells containing the DNA/lipid mixture were then incubated at 37 degrees C., 5 percent CO2 for about five hours. After incubation, 125 µl Optimem I supplemented with 20 percent FBS and 2× Penicillin/Streptomycin (0.1 unit/ml Penicillin, 0.1 µg/ml Streptomycin) (Life Technologies Inc., Gaithersburg, Md.) was added to stop the transfection. The following morning, the media was removed and a fresh medium containing high glucose DMEM, 10 percent PBS, and Pen/Strep was added, and the cells were allowed to recover for about 24 hours. Approximately 48 hours post transfection, fresh media was added and the cells were incubated for 6-8 hours. The medium from each well was then harvested, diluted 1:1 in Superblock (Pierce Inc., Rockford, Ill.), stamped into pre-coated ELISA plates and analyzed for the presence of A-beta as described below.

EXAMPLE III

Beta-Secretase Activity Assays with Cultured Cells

Beta secretase generates two forms of the A-beta peptide, a 40 amino acid form and a 42 amino acid form. In most people, about ninety percent of the A-beta is the 40 amino acid form, and about 10 percent is the 42 amino acid form. However, beta-amyloid plaques consist primarily of the 42 amino acid form, and in those individuals with familial Alzheimer's disease, there is a larger proportion of the 42 amino acid form as compared with the 40 amino acid form.

To analyze the level of A-beta in the cell culture medium obtained from each well of each plate, the following two assays were conducted on each medium.

A. Assay for Total Beta Amyloid Peptide

A monoclonal antibody against amino acids 17-24 of A-beta (Senetek Inc., St Louis, Mo., item number 220-10) referred to as m4G8, was diluted to a concentration of about 150 micrograms/ml in coating buffer (1.59 g/l $Na_2CO_3$, 2.93 g/l $NaHCO_3$, pH 9.69). About ninety microliters per well of coating buffer was then dispensed on to a polystyrene high binding 96 well flat-bottomed plate (Corning Costar, New York, N.Y.; item number 3590). About ten microliters per well of the m4G8 antibody diluted to about 150 micrograms/ml were added to the plate coating resulting in a final concentration of about 1.5 micrograms per well of m4G8. Each plate is then incubated overnight at 4 C on a plate mixer. The plates were then washed with wash buffer (7.1108 g/l Tris-HCl: $C_4H_{11}NO_3$—HCl, 0.5984 g/l Tris Base: $C_4H_{11}NO_3$, 8.766 g NaCl, 0.5 ml/l polyoxyethylene sorbitan monolaurate: $C_{11}H_{23}CO_2$) four times, and the non-specific binding sites were blocked with 300 microliters per well of Superblock TBS (Pierce Chemical Company, Rockford, Ill. 61105 item number 37535ZZ) for about three hours at room temperature.

The samples used for calibration were prepared from a commercially obtained solution of $Ab_{1-40}$, (5 micrograms/ml in DMSO; Quality Control Biochemicals, Inc, MA). The most concentrated sample was a 40,000 pg/ml solution, and was prepared by dilution into Superblock TBS (Pierce Chemical CO., Rockford, Ill. 61105). Sequential dilutions were then made in diluent to obtain 20,000, 10,000, 5,000, 2,500, 1,250, 625, 312.5, 156.25, 78.125 and 39.06 pg/ml.

One hundred microliters per well calibrators or 2.5 microliters per well of samples were applied to each well of each the microtiter plate; to each well was previously added one hundred microliters Superblock TBS plus m4G8 antibody. The plates were covered and incubated at about 4 C overnight with mixing after which they were washed four times with wash buffer at about 4 C.

To assess the amount of A-beta in each sample, the antibody m6E10-biotin raised against residues 1-17 of A-beta (Senetek Inc., St Louis, Mo., item number 340-10), was diluted to a final concentration of about 0.5 micrograms/ml into antibody diluent (Superblock TBS as described above) containing 2 percent normal mouse serum (Sigma Chemical Co., St. Louis, Mo.; item number S-3509) and 2 percent normal goat serum (Gibco/BRL, Grand Island, N.Y.; item number 16210-064). About 100 microliters of this diluted antibody were added to each well. The plate was covered and incubated for about 2 hours at 4 C with mixing. The plate was then washed four times with wash buffer at 4 C.

Europium labeled streptavidin (Wallac; Gaithersburg, Md.; item number 1244-360) was diluted 1:1000 in Assay Buffer (Wallac; item number 1244-106) to a final concentration of about 100 ng/ml. About one hundred microliters of this diluted streptavidin were then added to each well. Each plate was covered and incubated for about 1 hour at 4 C with mixing. Each plate was washed four times with wash buffer at 4 C after which about 100 microliters of Enhancement Solution (Wallac; item number 1244-105) was added to each well. The plate was then mixed for at least 5 minutes at room temperature.

Delfia time resolved fluorescence was read with a Wallac Victor 1420 multilabel counter using an excitation wavelength of 340 nm and an emission wavelength of 613 nm.

B. Assay for the 42 Amino Acid Form of A-Beta

A rabbit polyclonal antibody which specifically recognizes residue 42 of A-beta (Quality Controlled Biochemicals, MA 01748-2215; item number 44344) was diluted to about 2.5 micrograms/ml in the diluent Superblock TBS (Pierce Chemical Co. Rockford, Ill. 61105) and was added to each Reacti-Bind goat-anti-rabbit IgG-Fc specific plate (Pierce Chemical Co.; Rockford, Ill. 61105 item number NC1513). The plates were then incubated for about one hour at room temperature on a plate mixer with vigorous mixing. Following incubation, the plates were washed with wash buffer TBS-Tween (0.5 percent) four times, and the non-specific binding sites were blocked with about 100 microliters per well of Superblock TBS.

The standard curve samples were prepared from a stock solution of A-beta-1-42 peptide in DMSO at a concentration of 5 micrograms/ml. The highest standard was prepared at a final concentration of 40,000 pg/ml in Superblock TBS. Sequential dilutions were made using Superblock TBS to obtain final concentrations of 20,000, 10,000, 5,000, 2,500, 1,250, 625, 312.5, 156.25, 78.125 and 39.06 pg/ml.

About one hundred microliters per well of each standard, or 17.5 microliters per well of each sample was applied to each well of the microtiter plates to which about 100 microliters of Superblock TBS had been previously added. The plates were covered and incubated at about 4 C overnight with mixing. The plates were then washed four times with wash buffer containing about 0.5 percent TBS-Tween-20™ at 4 C.

Detection antibody, m4G8-biotin (Senetek; St. Louis, Mo.; item number 240-10) was diluted to about 0.5 micrograms per ml in a solution containing Superblock TBS, 2 percent normal mouse serum, 2 percent normal goat serum, and about 100 microliters of the diluted antibody were added to each well. Each plate was covered and incubated for about 2 hours at 4 C with mixing. Each plate was then washed four times with standard wash buffer at 4 C.

Europium labeled streptavidin (Wallac, Gaithersburg, Md.; item number 1244-360) was diluted 1:1000 in Assay Buffer (Wallac, Gaithersburg, Md.; item number 1244-106) to a final concentration of about 100 ng/ml. About one hundred μl per well were then added to each well. The plates were covered and incubated for about 1 hour at 4 C with mixing. Each plate was washed four times with wash buffer at 4 C, after which about 100 μl of Enhancement Solution (Wallac, Gaithersburg, Md.; item number 1244-105) were added to each well. Each plate was then mixed for at least 5 minutes at room temperature.

Delfia time resolved fluorescence was read with a Wallac Victor 1420 multilabel counter using an excitation wavelength of about 340 nm and an emission wavelength of about 613 nm.

EXAMPLE IV

Isolation of a Beta-Secretase cDNA

Approximately 864,000 independent clones were screened in the assays described above. Positive clones were selected based on the following two criteria:

1) increased A-beta 42 and/or total A-beta levels by more than two standard deviation points as compared with the plate average; and 2) selective skewing of the A-beta 42/total A-beta ratio towards A-beta 42 production.

Based on these criteria, about 144 putative positive pools of cDNAs were replated onto new master plates for a second round of analysis. An aliquot of the cDNA from each pool was transfected into 293T-APPsw101 (described above) using procedures described above. Transfections were conducted in duplicate. Those pools of cDNAs which consistently met positive clone criteria were subsequently replated and diluted from pools of about 100 clones to pools of about 20 clones and then to single clones. Single clones were diluted 1:10 into pCMVi vector DNA since the assumption was made that severe over-expression of a protease might result in toxicity to the cells.

One pool, termed A-11, exhibited a dramatic skewing of the A-beta 42/A-beta total ratio. In duplicate assays, this pool gave a ratio of about 0.8, and 1.0, respectively, whereas the plate average ratio for all plates ranged from about 0.5 to about 0.7. When A-11 was subsequently re-plated, it showed a modest yet consistent skewing of the A-beta 42/A-beta total ratio. In addition, A-11 had a standard deviation of greater than 2 for the increase in A-beta 42 levels over the plate average. The ratio skewing seemed to be somewhat dependent upon the density of cells at the time of transfection. When the cells were less dense at time of transfection, the skewing appeared to be more robust. As pool A-11 was broken down, it exhibited enhanced signal strength by both of the above criteria.

The results of the three assays for pool A-11 as well as the plate average are set forth below in Table II as total Europium counts. The data are presented as an average of duplicate transfections where each transfection was run in duplicate assays.

TABLE II

| Assay | Pool A-11 | Plate Average |
|---|---|---|
| Re-Arrayed Pool of 100 | | |
| A-beta 42 | 94,397 | 72,858 |
| Total | 177,356 | 164,334 |
| A-beta 42/Total | 0.53 | 0.44 |
| Pool of 20 | | |
| A-beta 42 | 178,212 | 133,402 |
| Total | 448,660 | 388,093 |
| A-beta 42/Total | 0.397 | 0.34 |
| Single Clone (β-Secretase) | | |
| A-beta 42 | 327,505 | 230,518 |
| Total | 295,438 | 363,141 |
| A-beta 42/Total | 1.1 | 0.63 |

When pool A-11 was diluted to single clones, several of these clones were sequenced using standard methods. All of the sequenced clones possessed an identical nucleotide sequence. After sequencing, one of these clones was inserted into the vector pCMVi-beta-secretase. Further sequence analysis indicated that the sequence possessed many sequence similarities to the aspartic protease family, and encoded a novel aspartic protease containing both a putative signal sequence and a transmembrane domain. The cDNA sequence of this aspartic protease, identified as a novel sequence encoding beta-secretase, is set forth in FIGS. 1A and 1B. The putative amino acid sequence as translated from the cDNA is set forth in FIG. 4, and this sequence possesses certain motifs characteristic of an aspartic proteases, such as two putative active site domains. The propeptide consists of amino acids 23-45. The signal peptide spans amino acids 1-22, and the transmembrane domain spans amino acids 461-477. The enzyme appears to be cleaved in vivo between amino acids 22 and 23 in some cases to remove the signal peptide, and in addition between amino acids 45 and 46 to remove the propeptide in other cases. The active site domains are believed to be amino acids 93-96 and 289-292. Hence, it is believed that the mature, active beta secretase enzyme spans amino acids 46-501. Based on computerized three dimensional structure analysis of human beta amino acid sequence, it is expected that the fragments 62-420, 73-420, 83-420, 90-420, 62-417, 73-417, 83-417, 90-417, 62-410, 73-410, 83-410, 90-410, 62-402, 73-402, 83-402, and 90-402 would all be biologically active.

EXAMPLE V

Identification of the Mouse and Rat Orthologs of Beta-Secretase

To identify the mouse and rat beta-secretase cDNAs, a FASTA search was performed using the full length human beta-secretase cDNA to search an Amgen database. For conducting this search, the scoring matrix used was GenRun-Data.fastadna.cmp, together with a constant pam factor. The Gap creation penalty and Gap extension penalty were set for 12.0 and 4.0, respectively. Four ESTs were identified, three for mouse and one for rat.

The three mouse sequences, which were 351 base pairs, 411 base pairs, and 364 base pairs in length were found to overlap. Thus, a complete mouse beta-secretase cDNA was obtained. This mouse cDNA was about 1923 base pairs in length and included about 95 nucleotides of 5 prime untranslated sequence, about 1503 nucleotides of open reading frame encoding 501 amino acids, and approximately 325 nucleotides of 3 prime untranslated sequence.

The single rat clone obtained encoded full length beta-secretase and was about 2158 nucleotides in length and contained 427 nucleotides of 5 prime untranslated sequence and 225 nucleotides of 3 prime untranslated sequence. The rat beta secretase is also 501 amino acids in length.

The full length mouse and rat beta-secretase cDNAs share approximately 93 percent and 91 percent identity, respectively, at the nucleic acid level with the human full length beta-secretase cDNA.

The mouse cDNA sequence containing only the full length coding region is set forth in FIGS. 2A and 2B (SEQ ID NO:2) and the corresponding amino acid sequence is set forth in FIG. 5 (SEQ ID NO:5).

The rat cDNA sequence containing only the full length coding region is set forth in FIGS. 3A and 3B (SEQ ID NO:3) and the corresponding amino acid sequence is set forth in FIG. 6 (SEQ ID NO:6).

EXAMPLE VI

Northern Blot Analysis of Beta-Secretase Transcripts

Northern blot analysis was performed to identify those tissues in which the beta-secretase transcript is present. A probe for use in Northern blot analysis was generated by digesting the human β-secretase cDNA with Pst I for about three hours at 37° C. and running the restriction digest on an 0.8 percent agarose gel to separate the fragments. The approximately 772 base pair ("bp") Pst I fragment extending from nucleotide 318 to nucleotide 1090 of the cDNA was isolated and gel purified using the QiaQuick® gel purification system (Qiagen, Chatsworth, Calif.). The isolated, gel pure fragment was quantitated by estimation on a one percent agarose gel. About 25 ng of this fragment was denatured by boiling for 5 minutes, and then quenching on ice for 2 minutes. The fragment was then radioactively labeled with alpha 32P-dCTP using the High Prime DNA labeling kit (Boehringer Manheim, Indianapolis, Ind.) according to the manufacturer's protocol. Human multiple tissue northern blots were purchased (Clonetech, Palo Alto, Calif.) and first prehybridized in Clontech Express™ hybridization buffer for about one hour at about 65° C. Following prehybridization, the labeled probe was denatured by boiling for about five minutes and quenching on ice for 2 minutes, and then added to the hybridization buffer containing the Northern blots. The blots were allowed to hybridize for about two hours at about 65° C. After hybridization the blots were washed in 2×SSC for 30 minutes at room temperature, followed by 3 successive washes in 0.2×SSC containing 0.1 percent SDS at about 60° C. for 30 minutes. The blots were dried briefly and exposed to autoradiography film for 72 hours at about −80° C.

The results are shown in FIG. 7. The lane contents are described in the Brief Description of the Figures. Three different RNA transcripts of approximately. 7 kb, 4.4 kb and 2.6 kb are apparent. All are of low abundance and expression is detected in most tissues. The highest levels are observed in pancreas and brain.

EXAMPLE VII

Beta-Secretase Protein Detection

An antibody to the carboxy terminus of beta-secretase was raised as follows. A synthetic peptide with the sequence CLRQQHDDFADDISLLK (SEQ ID NO:7) corresponding to amino acids 485-501 of beta-secretase was generated using standard methods (see below). The peptide was then conjugated to the carrier protein KLH by adding 5 mg of peptide to Pierce maleimide conjugation buffer (Pierce Chemical Co.; Rockford, Ill.; item number 77164), after which 0.5 ml of Pierce maleimide activated KLH (5 mg) (Pierce Chemical Co.; item number 77105) was added. The solution was incubated for about 2 hours at room temperature, and then run through a D-Salt™ Dextran column (Pierce Chemical Co.; item number C43233) to remove the EDTA. A one ml fraction from the column was mixed 1:1 with Titermax Research Adjuvant (CytRx Corp., Norcross, Ga.; item number R-10), prepared as an oil and water emulsion using 18 gauge double-hubbed needles (Popper and Sons, New Hyde Park, N.Y.) and loaded into 1 c.c. syringes fitted with 21 gauge needles. Three New Zealand White rabbits were each injected intramuscularly (IM) at two injection sites (0.05 ml per site). Four and six weeks later, the rabbits were boosted IM, again at two sites, 0.05 ml per site. The first sample bleed of 5 ml was drawn at 6 weeks. Two weeks later the second test bleed was drawn and tested for immunoprecipitation of β-secretase from transfected cells. The results indicated that a beta-secretase specific antibody had been generated.

The antibody was coupled to Protein A Sepharose using standard procedures for use in immunoprecipitation assays. The preimmune serum (negative control) was coupled in the same manner. Coupling was conducted as follows:

Protein A Sepharose CL-4B beads (Amersham Pharmacia Biotech, Inc, Piscataway, N.J.; item number 17-0780-01) were suspended at about 250 mg/ml in BSA/TBS (50 mM Tris-HCl, pH 7.5, 150 mM NaCl, 2% BSA). About 1 ml of the resuspended beads was mixed with about 250 µl of antiserum. The mixture was incubated at room temperature, rocking gently, for about one hour. The beads were then washed with about 10 ml of borate buffer (0.2 M sodium borate, pH 9.0). After about five minutes of gentle rocking, the mixture was spun at 3000 g for about five minutes and the supernatant was discarded. This washing procedure was then repeated, after which the beads were resuspended in about ten ml of borate buffer. Before adding the coupling agent, about 100 µl of the slurry was removed for gel electrophoresis analysis (tube A, see below).

The antiserum was then covalently coupled to the beads by adding about 50 mg of solid dimethyl pimelimidate (DMP, Pierce Chemical Co., Rockford, Ill.; item number 21666). The final concentration of DMP was about 20 mM and had a pH of at least 8.3. After incubating the mixture at room temperature for about thirty minutes with gentle rocking, a 100 microliter aliquot was removed (tube B, see below); the remainder of the mixture was spun at about 3000×g for about 5 minutes.

The coupling reaction was terminated by washing the beads in about 10 ml of 0.2 M ethanolamine, pH 8.0. After mixing, the solution was spun at about 3000×g for about 5 minutes. The beads were resuspended in about 10 ml of ethanolamine and incubated for about 2 hours at room temperature with gentle rocking. The beads were then spun at about 3000×g for about 5 minutes, after which the pellet was washed briefly with about 2 ml glycine (100 mM glycine, pH 3.0), followed by spinning again at about 3000×g for about 5 minutes.

The beads were rinsed with about 2 ml Tris (100 mM, pH 8.0) and spun at about 3000×g for about 5 minutes, after which the beads were resuspended in about 1 ml PBS containing 0.01 percent thimerosal. The beads were stored at 4° C. An aliquot (about 20 µl) of this final product (tube C) was run on SDS-PAGE gel along with tubes A and B (see above) to check the efficiency of coupling. The beads were prepared for SDS-PAGE by pelleting and resuspending them in about 30 µl of SDS sample buffer (Novex, San Diego, Calif.; item number LC2676), after which they were heated at about 85° C. for about 10 minutes and then run on a 10 percent Tris Glycine gel (Novex, San Diego, Calif.) at 100V for about 2-3 hours. The gel was and stained with Coomassie blue.

To evaluate the presence of beta-secretase in human brain tissue, human Alzheimer's disease and age-matched control brains were obtained from Sun Health Research Institute (Sun City, Ariz.) and homogenized according to the following protocol:

Pieces of parietal cortex of approximately 1 gram wet weight were finely chopped while frozen, and then placed in a Dounce glass homogenizer. Lysis buffer (50 mM Tris, pH 7.5, 150 mM NaCl, 1 percent NP-40, 12 mm CHAPS, 0.2 percent BSA, 2 mM EDTA, 20 mM PMSF, 10 µM leupeptin, 1 µM pepstatin A, 2 µg/ml aprotinin, 0.1 mM Pefabloc) was added in a proportion of 2 ml buffer per 1 g brain tissue, and the mixture was homogenized using 50 strokes with a tight fitting plunger. The homogenate was spun at 20,000×g for about 10 minutes at 4° C. The supernatant was used for the immunoprecipitation and Western blotting as described below. Remaining material was stored at −80° C. The supernatant concentration was assumed to be approximately 500 mg protein/ml based on the starting wet weight.

The supernatants were immunoprecipitated as described immediately below with either the antibody or with preimmune serum coupled to protein A Sepharose (prepared as described above), separated on SDS-PAGE, and Western blotted with the pooled antisera. As a positive control, lysates made from 239T-APPsw101 cells described above transiently transfected with the full length beta-secretase expression construct were analyzed under the same conditions.

For each immunoprecipitation, about 50 µl of brain supernatant prepared as described above (about 25 mg wet weight equivalent) or the lysate made from 101 cells transiently transfected with the beta-secretase expression construct (about ½₀ of the volume of each dish) were used. The brain supernatant and the lysate were precleared in bulk (about 100 µl homogenate containing about 25 µl Protein A Sepharose) by incubating at about 4° C. for 30 minutes with gentle rocking. The tubes were centrifuged at about 960×g for about 5 minutes. The supernatants (about 50 µl) were immunoprecipitated with about 40 µl of the Protein-A-beta-secretase antisera or Protein-A-preimmune serum. The volume of the immunoprecipitation was brought up to about 500 µl with TBS (50 mM Tris, pH 7.5, 150 mM NaCl) and the reaction was carried out at about 4° C. for about 3 hours with rocking. The beads were pelleted at about 960×g for about 5 minutes and washed three times with STEN buffer (1×STEN=50 mM Tris-HCl, pH 7.5, 150 mM NaCl, 2 mM EDTA, 0.2 percent NP-40) for about 15 minutes at about 4° C. with rocking. The beads were pelleted after each wash at about 960×g for about 5 minutes. The first wash buffer was 0.5 M STEN (1×STEN+ 0.5 M sodium chloride, 5 µg/ml leupeptin, 5 µg/ml aprotinin). The second wash buffer was SDS-STEN (1×STEN+0.1% SDS, 5 µg/ml leupeptin, 5 µg/ml aprotinin), and the third wash buffer was 1×STEN. After washing, about 15 µl of SDS-Sample Buffer (Novex, San Diego, Calif.; item number LC2676) was added and the samples were stored at −20° C. overnight.

The samples were heated at about 95° C. for about 5 minutes and loaded onto a 10-20 percent Tris-Tricine gel (Novex San Diego, Calif.; item number EC6625). The gel was run at 100V for 2-3 hours and then transferred to PVDF (Novex, San Diego, Calif.; item number LC2002) using the Bio Rad Trans Blot Cell at about 400 mA for about 2 hours at 4° C. in a solution of 200 mM glycine, 25 mM Trizma base and 20 percent methanol.

The Western blot was then analyzed for the presence of beta secretase as follows. The Western blot was wetted in methanol for about 30 seconds then rinsed with TBST (10 mM Tris-HCl, pH 8.0, 150 mM sodium chloride, 0.05 percent Tween-20) before blocking with 5 percent dry milk in TBST for about one and one-half hours at room temperature, with rocking. The Western blot was incubated with primary beta-secretase antibody (prepared as described above) that had been diluted about 1:1000 in PBS containing 1 percent BSA and 0.1 percent Tween-20. Incubation was overnight at about 4° C. with rocking. After incubation, the Western blot was washed three times in TBST for about 5 minutes per wash with rocking at room temperature.

The secondary antibody used to detect beta-secretase antibody was alkaline phosphatase conjugated Goat Anti-rabbit IgG (Promega, Madison, Wis.; item number S373B). This antibody was diluted at about 1:7500 in alkaline phosphatase buffer (100 mM Tris-HCl, pH 9.2, 100 mM sodium chloride, 5 mM $MgCl_2$) and added to the Western blot. After about 30 minutes of incubation at room temperature, the Western blot was washed as described above and developed about 5-10 minutes with BCIP/NBT (Kirkegaard and Perry Labs, Gaithersburg, Md.; item number 50-81-08). To stop development, the Western blot was rinsed in stop solution (20 mM Tris-HCl, pH 8.0, 5 mM EDTA) and dried.

Figure 8:
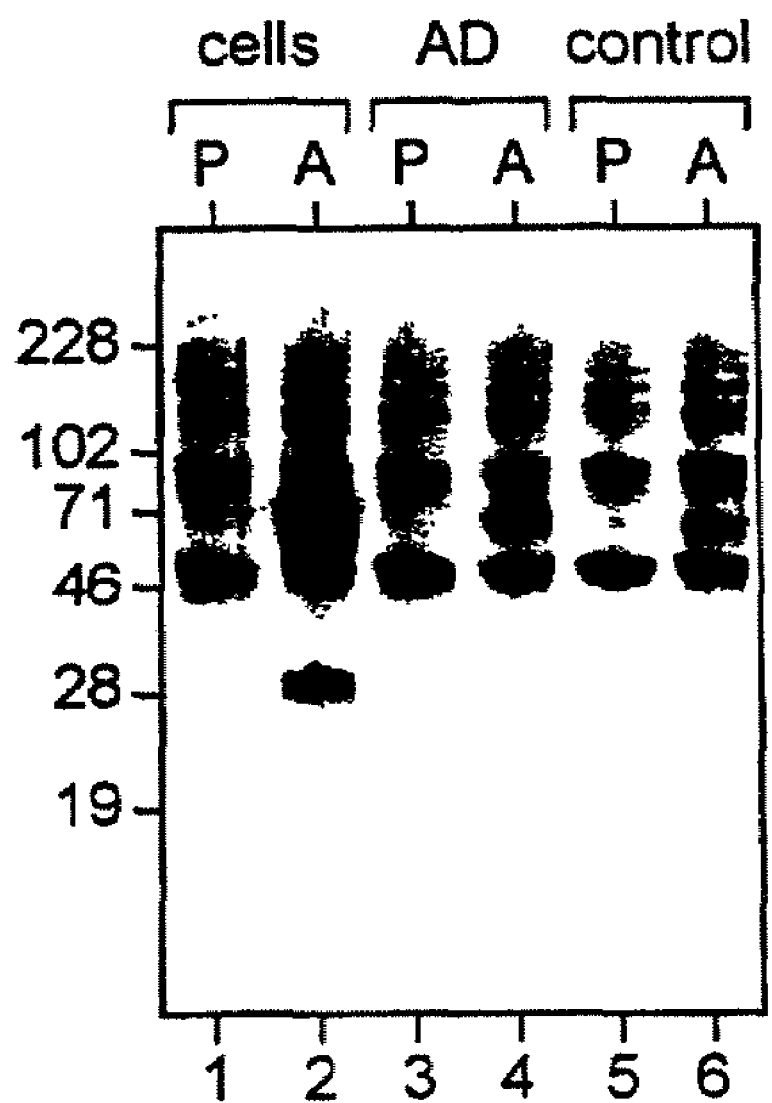
FIG. 8 depicts a Western blot of a SDS gel containing protein from either human 293 cells transfected with beta-secretase cDNA or human brain. Lane 1 contains high molecular Weight standards; lane 2 contains immunoprecipitate of cell culture medium from human 293 cells transiently transfected with beta-secretase cDNA using preimmune serum; lane 3 contains immunoprecipitate of cell culture medium from human 293 cells transiently transfected with beta-secretase cDNA using beta-secretase antibody; lane 4 contains immunoprecipitate of homogenate from human Alzheimer's disease brain tissue using preimmune serum; lane 5 contains immunoprecipitate of homogenate from human Alzheimer's disease brain tissue using antibody against beta-secretase; lane 6 contains immunoprecipitate of homogenate from human control (non-Alzheimer's disease) brain tissue using preimmune serum; lane 7 contains immunoprecipitate of homogenate from human control (non-Alzheimer's disease) brain tissue using antibody against beta-secretase; lane 8 contains low molecular weight standards.

The results are shown in FIG. 8. "P" represents immunoprecipitations with preimmune serum, and "A" represents immunoprecipitations with anti-beta secretase antibody. "Cells" refers to human cultured cells transfected with the human beta-secretase cDNA; "AD" refers to brain tissue homogenate from Alzheimer's disease patients; and "Control" refers to brain tissue homogenate from normal people. As can be seen, a major band of approximately 70 kilo daltons is apparent in lane 2. A band of approximately the same molecular weight is present in lanes 4 and 6 as well. This result indicates that the transfected cells are expressing the beta secretase protein which is observed in human brain. The molecular weight of beta-secretase calculated from the amino acid sequence is about 55.8 kilo daltons, suggesting that the protein expressed in cells and brain could be glycosylated.

EXAMPLE VIII

Preparation of a Human Beta-Secretase Mutant

A hemagglutinin (HA) epitope tag was added in frame to the C-terminus of the full length beta-secretase cDNA for the purpose of detection with the monoclonal anti-HA antibody HA.11 (obtained from BabCo, Berkeley Calif.). The HA epitope tag consists of 11 amino acids and was used as a marker tag, enabling the surveillance of the beta-secretase-HA fusion polypeptide via anti-HA antibody detection.

The C-terminal HA tagged form of beta-secretase was generated by PCR in two steps. For the first step, the forward primer had 5 prime to 3 prime sequence corresponding to nucleotides 1047-1070 of the beta-secretase cDNA and had the sequence:

(SEQ ID NO:8)
TGACTCTCTGGTAAAGCAGACCCA

The reverse primer for this first round of PCR corresponded to nucleotides 1938-1957 of beta-secretase together with the first 18 base pairs of the HA tag and had the sequence:

(SEQ ID NO:9)
AGGCACGTCGTAAGGGTACTTCAGCAGGGAGATGTCA

The PCR conditions for this reaction were: 97 C for 60 seconds; 97 C for 30 seconds, 60 C for 30 seconds and 72 C for 1 minute for twenty five cycles. This round of PCR generated a 928 base pair product. This PCR product was then purified using the Wizard™ PCR Preps DNA Purification System (Promega, Madison, Wis.). This PCR product was then used as template for the second PCR reaction. This reaction used the identical forward primer and a reverse primer corresponding to all 11 amino acids of the HA tag followed immediately by a termination codon and a BglII restriction site. This primer had the sequence:

(SEQ ID NO:10)
TGAAGATCTTCATCCGCTGGCATAATCAGGCACGTCGTAAGGGTA

PCR conditions for this reaction were identical to those used for the first reaction. The 955 base pair PCR product that resulted from this second round of PCR was purified as described above and digested with BsrGI and BglII overnight at 37 C. The digested fragment was gel purified from a 0.8 percent agarose gel using the QiaQuick gel purification system (Qiagen, Chatsworth, Calif.) and subsequently subcloned into BsrGI/BglII digested pCMVi-beta-secretase.

A mutant DNA construct encoding D93A human beta secretase was prepared via PCR. Each fragment contained the D93A mutation and 24 base pairs of overlapping sequence. The first or forward fragment contained the D93A mutation in the sense orientation at the extreme 3 prime end of the fragment, while the second or reverse fragment contained the D93A mutation at the extreme 5 prime end of the fragment in the antisense orientation. Next, these PCR products were purified and combined together (at equimolar ratio) in a second amplification reaction using just the two outer primers for amplification, thus giving rise to a full length double stranded 953 bp BamHI-BsrGI 008 fragment of beta secretase containing the D93A mutation. This PCR product was then subsequently used to replace the BamHI-BsrGI fragment of the native beta-secretase cDNA.

The forward first step PCR product was generated using a 5 prime forward primer which is identical to bases 211-233 of the beta-secretase cDNA sequence. This primer has the sequence:

(SEQ ID NO:11)
GTGCCGATGTAGCGGGCTCCGGA

A 3 prime reverse primer was generated which corresponds to bases 720-743 of human beta-secretase cDNA except that the T at position 731 was changed to G thus changing the aspartic acid residue at position 93 of the peptide sequence to an alanine residue (on the antisense strand). This primer has the sequence:

(SEQ ID NO:12)
CTGCTGCCTGTAGCCACCAGGATG

The reverse first step PCR product was generated using a 5 prime forward primer in which the A at base 731 was changed to a C, thereby creating a construct that encoded an alanine at position 93 of the human beta-secretase polypeptide sequence (on the sense strand). This primer has the sequence:

CATCCTGGTGGCTACAGGCAGCAG (SEQ ID NO:13)

The 3 prime reverse primer used in this PCR reaction is identical to bases 1230-1254 of the beta secretase human cDNA. This primer has the sequence:

CACCCGCACAATGATCACCTCATAA (SEQ ID NO:14)

PCR reactions for the forward first step reaction were conducted in an MJ Research PTC 200 thermal cycler (MJ Research, Watertown, Mass.) using the following conditions: 97 C for 90 seconds; 98 C for 30 seconds, 60 C for 30 seconds and 72 C for 1 minute for twenty five cycles. The two PCR products were then purified using the Wizard™ PCR Preps DNA Purification System (Promega, Madison, Wis.).

For the second step PCR reaction, the two PCR fragments generated above were added in an approximately equimolar ratio, and were subsequently amplified using the following primers:

GTGCCGATGTAGCGGGCTCCGGA (SEQ ID NO:15)

CACCCGCACAATGATCACCTCATAA (SEQ ID NO:16)

The PCR conditions for this reaction were identical to those used in the first step reactions. The PCR products were purified using the Wizard™ PCR Preps DNA Purification System (Promega, Madison, Wis.), restriction digested with BamHI and BsrGI and gel purified on a 0.8 percent agarose gel using the QiaQuick gel purification system (Qiagen, Chatsworth, Calif.). This fragment was then subcloned into the BamHI/BsrGI digested pCMVi-beta-secretase/HA tag construct.

In a separate procedure, the human APP-695 cDNA was subcloned into the CMV based expression vector pCMVi (Cell & Molecular Technologies Inc., LaVallette, N.J.) as a HindIII-Not1 fragment to generate the vector pCMVi-AP-Pwt. A derivative of 293 cells containing the SV40 large T antigen (Cell & Molecular Technologies, LaVallette, N.J.) maintained in high glucose Dulbecco's modified Eagle's medium (DMEM) supplemented with 10 percent fetal calf serum was co-transfected with pCMVi-APPwt and pRSV-Puro by the calcium phosphate method as described (Gorman et al., supra). Transfected cells were cultured in medium containing puromycin at a concentration of about 5 micrograms/ml. Puromycin resistant colonies were selected about 48 hours after transfection. Fourteen days later, individual resistant colonies were isolated, expanded, and analyzed by Western dot blot for APP expression using the monoclonal antibody 22C11 (Boehringer Manheim Corp.) which recognizes secreted APP.

One positive colony was expanded to generate a cell line referred to as "293T/APPwt".

To assess the activity of the D93A mutant, 293T/APPwt cells were transfected with beta-secretase cDNA (either wild type or D93A mutant) or with control plasmid (no beta-secretase insert) as follows.

The 293T/APPwt cells were plated out at a density of about $2.8 \times 10^5$ cells per well in a 6-well tissue culture plate (Falcon) and grown for 2 days at 37° C. in an atmosphere of about 5 percent $CO_2$. The cells were transfected the morning of day 3. Prior to transfection, all plasmids to be used were resuspended in water. Two polystyrene tubes were set up for each well. One tube received about 3 μg total DNA (control plasmid was diluted 1:10 as compared with the plasmids containing beta-secretase inserts) and 1 ml of Opti-MEM I reduced serum media (Gibco-BRL, Grand Island, N.Y.). The second tube received about 14 μl DMRIE-C (Gibco-BRL) and 1 ml Opti-MEM I. The tubes were then mixed together and incubated at room temperature for about 30 minutes. The media was then removed from the cells and the DNA/DMRIE-C/Opti-MEM I mixture (2 ml total volume) was added to each well. The cells were incubated at about 37° C. in about 5 percent $CO_2$ for about 5 hours. Following the incubation, about 2 ml of Opti-MEM I containing 20 percent fetal bovine serum (Gibco-BRL) were added to each well of cells, after which the cells were incubated at about 37° C., in an atmosphere of about 5 percent $CO_2$ overnight. The following morning (day 4) the media was removed and 2 ml of fresh DMEM containing 10 percent fetal bovine serum (Gibco-BRL) were added, and the cells were then incubated at about 37° C. in an atmosphere of about 5 percent $CO_2$ overnight. The following day (day 5) the conditioned media was collected, and sodium dodecyl sulfate (Sigma, St. Louis, Mo.) was added to a final concentration of about 0.1 percent. The samples were stored at about −80° C.

Figure 9A:
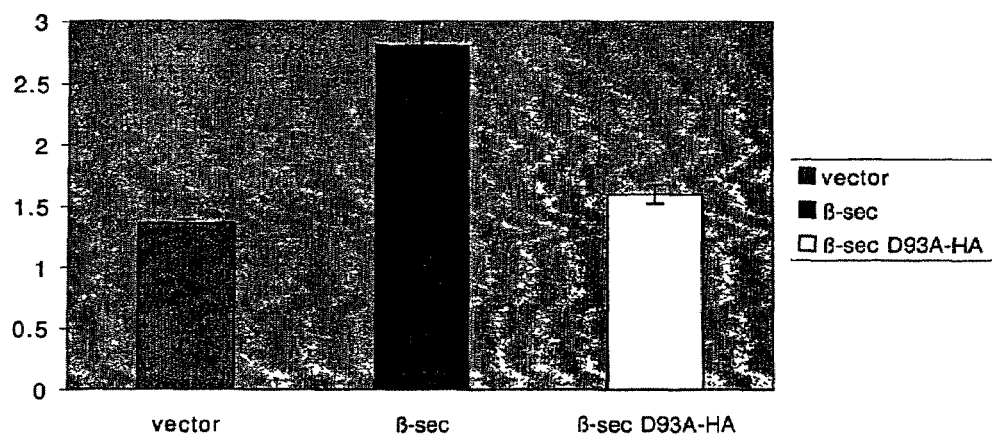
FIG. 9A depicts a graph of ELISA assays to detect A-beta 42. APP expressing cells were transfected with either vector plasmid (negative control), the beta-secretase vector (positive control), or beta-secretase vector containing the D93A mutation.
Figure 9B:
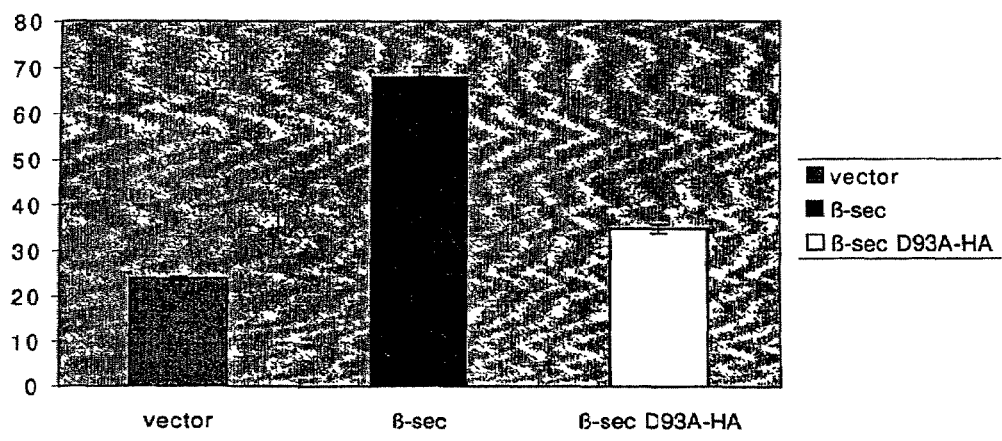
FIG. 9B depicts graph of ELISA assays to detect A-beta 40. APP expressing cells were transfected with either vector plasmid (negative control), the beta-secretase vector (positive control), or beta-secretase vector containing the D93A mutation.

FIGS. 9A and 9B show the results of the transfection. Conditioned media of cells transfected with the wild type beta-secretase expression plasmid contain significantly higher levels of A-beta 42 (FIG. 9A) and A-beta 40 (FIG. 9B) than conditioned media of cells transfected with either the control plasmid or conditioned media of cells transfected with the beta-secretase D93A-HA mutant. This suggests that D93 is part of the active site of human beta-secretase.

EXAMPLE IX

Purification of Soluble Beta Secretase-Fc Fusion Polypeptide

A human IgG1 Fc gene (the sequence of which is set forth in Genbank as accession number X70421) was amplified by polymerase chain reaction and subcloned into the vector pBluescript SK- (Stratagene, La Jolla, Calif.). PCR was conducted using a MJ Research PTC-200 thermal cycler for 25 cycles with the following parameters: 94 C for 1 minute; 55 C for 1 minute; and 72 C for 1 minute. The polymerase used was Pfu polymerase (Stratagene, La Jolla, Calif.). The following primers were used as forward and reverse primers, respectively for this PCR reaction:

CGGGATCCGGTCACCGACAAAACTCACACA (SEQ ID NO:20)

GCTCTAGAAGCTTCTGCAGGTCGACTCATTTACCCGGAGA (SEQ ID NO:21)

The forward primer incorporated 5' BamHI and BstEII sites at the 5' end of the PCR product, and the reverse primer incorporated SalI, PstI, HindIII, and XbaI sites at the 3' end of the 723 base pair PCR fragment that was generated using these primers. The PCR fragment was purified using Qiaquick™ purification kit (Qiagen, Chatsworth, Calif.), and digested with BamHI and XbaI. After a second round of gel purification, the PCR fragment was ligated into the vector pBluescript SK- (Stratagene, La Jolla, Calif.) that was previously digested with BamHI and XbaI.

An 1195 base pair fragment of the human beta-secretase cDNA (nucleotides 276 to 1471) was excised from the full length cDNA by digestion with EcoRI and BsrGI and gel purified. This fragment contained the 5' untranslated region and the coding region up to amino acid 245 of the human beta secretase cDNA. A second fragment of human beta-secretase cDNA encoding amino acids 246 to 460 (ending exactly at the start of the putative transmembrane domain) was amplified by PCR using procedures described above for the IgG1 fusion gene. Amplification forward and reverse primers for this reaction were as follows:

```
                                                (SEQ ID NO:22)
    CGACCACTCGCTGTACACAGGCAG (SEQ ID NO:23)
    GTCGGTGACCGCATAGGCTATGGTCATGAGGGT
```

The forward primer incorporated the endogenous 5' BsrGI site, and the reverse primer incorporated a 3' BstEII site for in-frame ligation of the PCR product into the IgG1 fusion gene cassette. The resulting 672 base pair PCR fragment was purified using the Qiaquick™ purification kit (Qiagen, Chatsworth, Calif.), digested with BsrGI and BstEII, and gel-purified.

Separately, the human IgG1 fusion cassette was digested with EcoRI and BstEII and gel-purified. A 3-way ligation was then conducted by combining the 1195 base pair EcoRI/BsrGI human beta-secretase fragment and the 672 base pair BsrGI/BstEII beta secretase PCR fragment with the EcoRI/BstEII human IgG1 fusion cassette. The completed beta secretase fusion gene was called beta-secretase-Fc and contained 3 additional amino acids (alanine-valine-threonine) at the junction between the beta-secretase and IgG1 coding regions.

The beta-secretase-Fc fusion gene was excised from the plasmid pBluescript SK- by digestion with XhoI and NotI, and gel-purified. The mammalian expression vector pCMVi (Cell & Molecular Technologies Inc. Lavallette, N.J.) was also digested with the same enzymes and gel-purified, after which the beta-secretase-Fc fusion gene fragment was ligated into the XhoI/NotI digested pCMVi vector.

Human embryonic kidney 293T cells (Cell & Molecular Technologies Inc., Lavallette, N.J.) stably transfected with the beta-secretase-Fc fusion construct by the standard calcium phosphate method (Gorman et al, *DNA Prot. Eng. Tech.* 2: 3-10 [1990]) were conditioned for either four or five days in Opti-Mem reduced serum medium (GibcoBRL, Grand Island, N.Y.; item number 31985). After filtration with a 0.45 µm filter, conditioned media was concentrated and buffer exchanged to column equilibration buffer (PBS containing 2 mM Chaps). The concentrated conditioned medium was then loaded onto a one milliliter recombinant protein A column (Amersham Pharmacia Biotech, Inc, Piscataway, N.J.; item number 17-5079-02) which had been pre-equilibrated with 10 column volumes of PBS containing 2 mM Chaps™ at about 4 C. After loading the sample on the column, the column was washed with 10 column volumes of column equilibration buffer, and the beta-secretase-Fc fusion protein was eluted from the column with a step gradient to 100 mM Sodium Citrate, pH 2.8 containing 2 mM Chaps™. One milliliter fractions were collected. Before collection, fraction collection tubes were loaded with 300 ml of 1 M Tris base, pH 9.2, to neutralize fractions upon elution. Final pH of each 1.3 ml fraction was approximately pH 7.5. Fractions containing beta-secretase-Fc fusion polypeptide were pooled, concentrated, and buffer exchanged to TBS containing 2 mM Chaps for storage.

Figure 10:
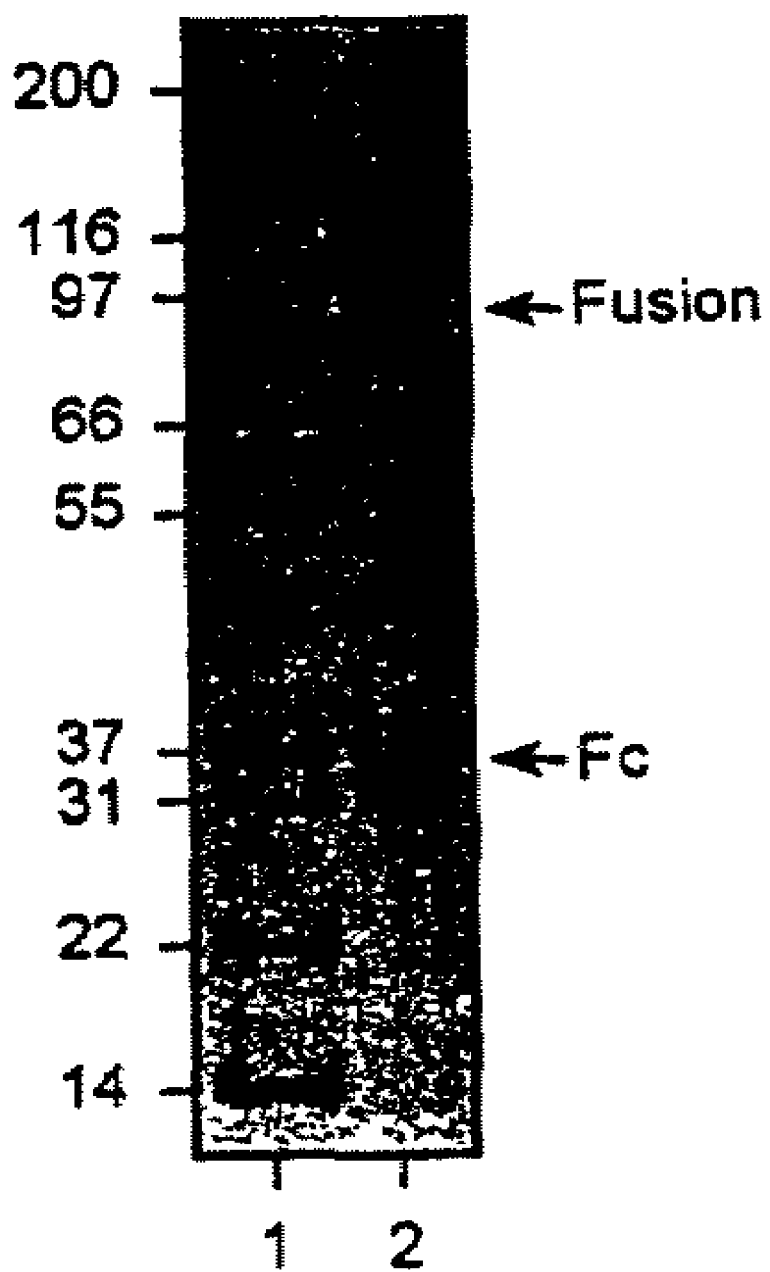
FIG. 10 depicts an SDS gel of purified human beta-secretase prepared as an Fc fusion. The beta-secretase-Fc fusion is indicated as "fusion" in Lane 2; "Fc" refers to an Fc fragment only. Molecular weight markers are indicated in Lane 1.

FIG. 10 shows a Coomassie stained SDS gel of the purified beta-secretase-Fc fusion protein (lane 2) alongside molecular weight markers (lane 1). Only the beta-secretase-Fc fusion polypeptide and some cleaved Fc polypeptide were detectable. The predicted molecular weight of the fusion protein is 76.8 kilo daltons. The higher observed molecular weight is presumably due to glycosylation.

EXAMPLE X

Beta-Secretase Activity Assay

Recombinant native as well as mutant beta secretase polypeptides were assayed for activity by measuring the ability of the molecule to cleave various A-beta peptides.

All peptides were synthesized by the Fmoc (fluorenylmethoxycarbonyl)/t-butyl based solid phase peptide chemistry method using standard procedures. An ABI 431A peptide synthesizer (Perkin Elmer Corp., Foster City, Calif.) was used with a single coupling program to carry out the chain assembly. Commercially available preloaded Fmoc-AAA-HMP derivatized polystyrene resin (Midwest Biotech, Fishers, Ind. or Calbiochem, San Diego, Calif.) was used to prepare the C-terminal amino acid. Subsequent amino acids were coupled in 20 fold excess as HOBT (hydroxybenztriazole) esters using carbodiimide activation. The side-chain protecting groups for each amino acid were as follows: Arg (Pbf; 2,2,4,6,7-pentamethyldihydrobenzofuran-5-sulfonyl), Asn (Trt; trityl), Asp (OtBu; O-tert-butyl), Cys (Trt; trityl), Cys (Acm; acetamidomethyl), Gln (Trt; trityl), Glu (OtBu; O-tert-butyl), His (Trt; trityl), Lys (Boc; tert-butoxycarbonyl), Ser (tBu; tert-butyl), Thr (tBu), and Tyr (tBu; tert-butyl). Upon removal of the final N-terminal Fmoc with 20 percent piperidine in N-methylpyrrolidone, side-chain protecting groups were then removed and the peptide(s) were cleaved from the resin by treatment with TFA (trifluoroacetic acid):triisopropylsilane:water (92.5, 2.5, 5 v/v) for about 4 hours. The resulting suspension was filtered, and the filtrate volume reduced by roto-evaporation. The crude peptides were precipitated and washed with ether, followed by drying in-vacuo.

The linear (fully reduced) peptide intermediates were purified by HPLC prior to either an equilibrium oxidative refold or a two step oxidative cyclization process. The connectivity of those peptides containing one or two disulfides is unambiguous as a result of using orthogonal cysteine protection and oxidative-cyclization methods as follows. The first disulfide bond was formed using air oxidation (Cys[Trt] protection) and the second disulfide bond was formed by iodine treatment on the bis-Cys(Acm) containing-cyclic peptide intermediate. For the two peptides containing three disulfide bridges, oxidation was carried out using 10 percent DMSO (dimethylsulfoxide) oxidation under acidic conditions.

Each crude peptide was dissolved in 8M guanidine containing 100 mM DTT (dithiothreitol) and purified to at least 95 percent homogeneity by preparative reverse-phase HPLC using a Vydac C18 (2.5 cm×25 cm) column (Vydac Corp., Hesperia, Calif.) with a linear gradient of 0.1 percent TFA (v/v) in water and 0.05 percent TFA (v/v) in acetonitrile.

The composition of each peptide was assessed using electro-spray ionization (ESI) mass spectrometry and amino acid analysis. Mass spectra for each synthetic peptide was obtained on a Sciex API (Perkin Elmer Corp., Foster City, Calif.) single quadropole mass spectrometer, and reported as m/z (M+1). All mass spectral samples were obtained as fractions off of the preparative HPLC purification.

Amino acid analyses of each peptide were performed on an ABI 420A hydrolyzer/derivatizer (ABI, Foster City, Calif.) using a 130A separation system (ABI, Foster City, Calif.). The peptides were hydrolyzed using 6N HCl at 200° for 30 minutes and then derivatized using the defined instrument protocol in the ABI AAA420A Operator's Manual as PTC (phenylisothiocynate) derivatives. The amino acid mixture was then separated by HPLC on a Brownlee PTC C18 column (ABI, Foster City, Calif.), 5 micron pore size, 2.1×220 mm, with a linear gradient of water and acetonitrile. Both solvents were buffered with sodium acetate to a pH of about 5.4. The amino acid composition of each peptide was then determined by comparison of the unknown peak ratios with an equimolar amino acid standard. Each peptide generated experimental data that conformed with expected theoretical values.

The sequence of the synthesized peptides (from amino to carboxy terminus) is set forth in Table III below:

TABLE III

| Peptide | Peptide Sequence | |
|---|---|---|
| Sw | EVNLDAEF | SEQ ID NO: 17 |
| WT | EVKMDAEF | SEQ ID NO: 18 |
| MV | EVKVDAEF | SEQ ID NO: 19 |

To facilitate analysis of the assays, all of the peptides were labeled with dinitrophenol (DNP) at the amino terminus.

DNP was incorporated during synthesis of the peptide substrates as dnp-glutamic acid.

Each assay was conducted as follows. The purified beta secretase-Fc (amounts indicated in FIG. 11) was combined separately with each peptide substrate (20 μM) to a final volume of about 50 μl in a buffer containing 50 mM acetic acid, 50 mM Mes, 100 mM Tris, pH 5.0 and 0.05 percent (w/v) Thesit. The samples were incubated at ambient room temperature for about 6 hours. At the end of the incubation period, reaction mixtures were quenched by addition of about 200 μl of 5 percent (v/v) trifluoroacetic acid (TFA). Quenched reactions were analyzed by HPLC on a 5 μm, C18 reversed-phase column (Sephasil Peptide, 4.6×100 mm; Amersham Pharmacia Biotech, Piscataway, N.J.) using first a linear gradient of 18-31.5 percent acetonitrile in 0.1 percent TFA over 40 minutes, then 31.5-81 percent acetonitrile for 1 minute, then 81 percent acetonitrile for 4 minutes, and then returning to 18-percent acetonitrile for several minutes to reequilibrate the column. The linear 18-31.5 percent acetonitrile gradient was subsequently modified to a concave gradient (curve 7 as defined by the Dionex Pubs 40 pump system, Dionex Corporation, Sunnyvale, Calif.) from 18-31.5 percent acetonitrile in 15 minutes. Proteolysis of the Sw and WT octapeptides was evaluated using a linear gradient of 27-37.8 percent acetonitrile over 24 minutes on the same column.

Both product and substrate were monitored by absorbance at 360 nm. Products were typically identified by retention time comparison with appropriate substrate peptides run under identical conditions. The rate of product formation or the amount of product formed was determined by comparison of the area under the product peak to a standard curve of authentic peptide. The reference product peptides were each labeled with dinitrophenol at the amino terminus, and had the sequences:

| | |
|---|---|
| EVNL | (SEQ ID NO:24) |
| EVKV | (SEQ ID NO:25) |
| EVKM | (SEQ ID NO:26) |

The concentration of standard was determined from the extinction coefficient of DNP ($e_{365nm}$=16 mM$^{-1}$cm$^{-1}$). The HPLC assay was linear and reproducible from approximately 25 to about 300 pmol of product.

Figure 11:
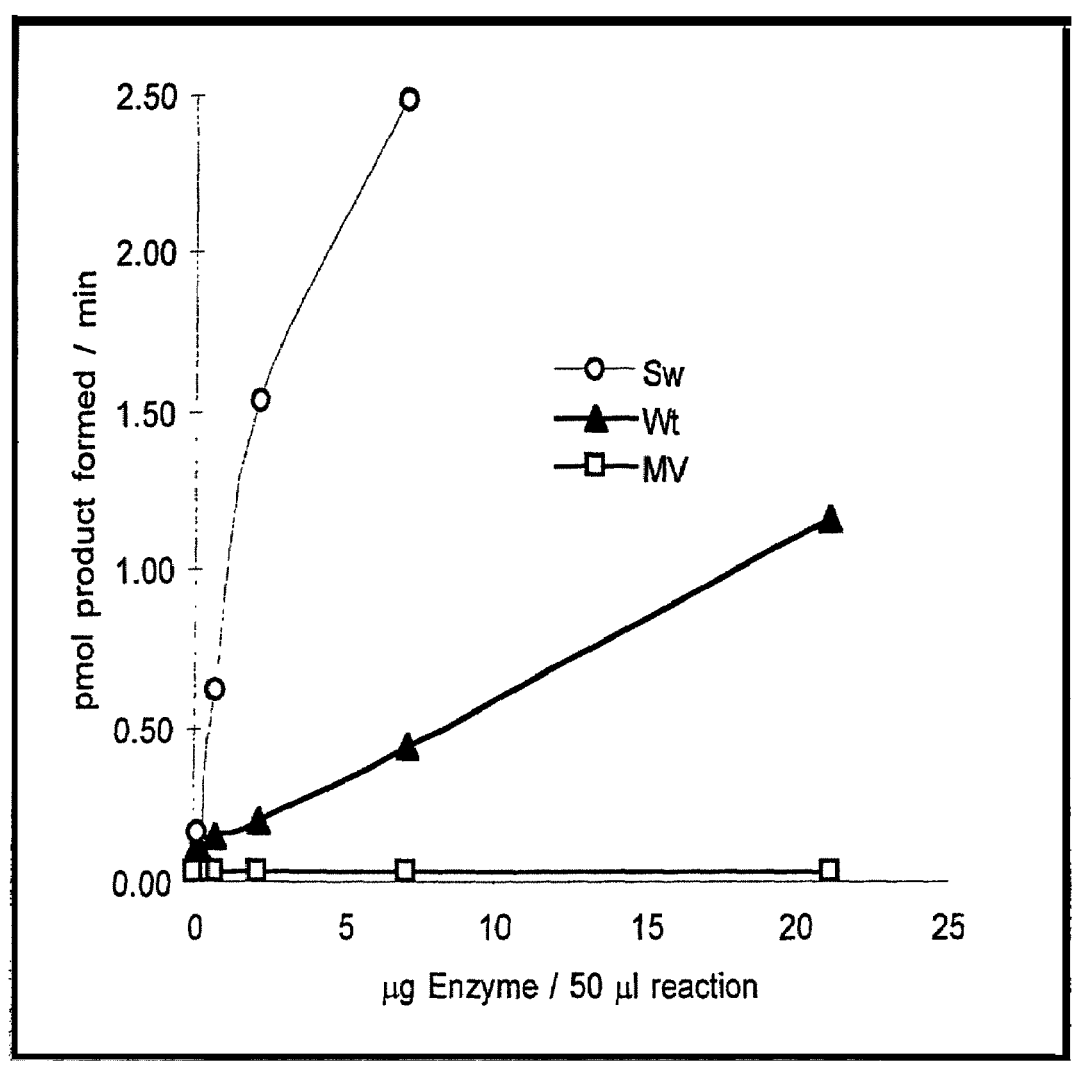
FIG. 11 is a graph depicting the ability of human beta-secretase-Fc fusion to cleave various APP peptides. The X-axis is the amount of enzyme in the reaction mixture and the Y-axis is the amount of cleavage (denoted as pmol product formed) of each of three substrate peptides. "Sw" refers to the APP peptide with the Swedish mutation; "Wt" refers to wild type APP peptide; and "MV" refers to a mutated APP peptide.
Figure 12:
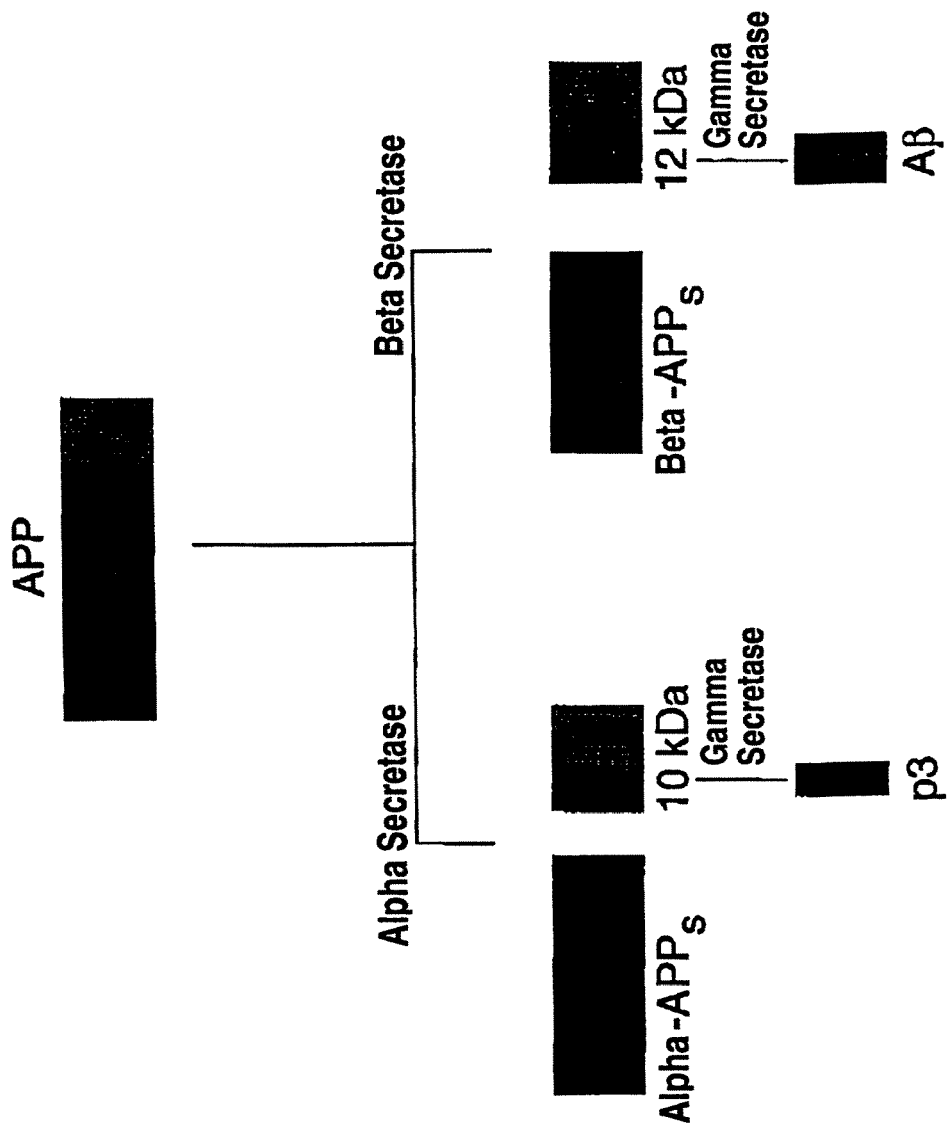
FIG. 12 is a schematic representation of the processing steps of beta-APP to generate A-beta. APP can undergo cleavage by alpha-secretase to form a secreted alpha-APP soluble fragment ("alpha-APPS") and a membrane bound fragment of about 10 kDa. The membrane bound fragment can then be cleaved by gamma-secretase to release a fragment referred to as "p3". Alternatively, APP can undergo beta-secretase cleavage to release a soluble fragment referred to as "beta-APPs" and a membrane bound fragment of about 12 kDa. The membrane bound fragment can then be cleaved by gamma-secretase to release A-beta.

The results are shown in FIG. 11 for each substrate. As can be seen, the Swedish substrate (Sw) is clearly preferred by the enzyme over the wild type (Wt) substrate which is preferred over the methionine to valine mutant (MV) substrate. These results indicate that purified beta-secretase-Fc has the same substrate specificity that has previously been described for beta-secretase from intact cells (Citron et al., Neuron 14:661-670 91995]).

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. An isolated biologically active beta-secretase polypeptide, wherein the polypeptide is encoded by the DNA vector insert of ATCC Deposit No. 207159.

\* \* \* \* \*